(12) United States Patent
Burdette et al.

(10) Patent No.: US 11,896,779 B2
(45) Date of Patent: Feb. 13, 2024

(54) MRI COMPATIBLE ABLATION CATHETER SYSTEM INCORPORATING DIRECTIONAL HIGH-INTENSITY ULTRASOUND FOR TREATMENT

(71) Applicant: ACOUSTIC MEDSYSTEMS, INC., Savoy, IL (US)

(72) Inventors: Everette C. Burdette, Savoy, IL (US); Bruce M. Komadina, Urbana, IL (US); Emery M. Williams, Champaign, IL (US)

(73) Assignee: Acoustic Medsystems, Inc., Savoy, IL (US)

( * ) Notice: Subject to any disclaimer, the term of this patent is extended or adjusted under 35 U.S.C. 154(b) by 187 days.

(21) Appl. No.: 17/084,050

(22) Filed: Oct. 29, 2020

(65) Prior Publication Data
US 2021/0178121 A1    Jun. 17, 2021

Related U.S. Application Data

(63) Continuation of application No. 14/421,902, filed as application No. PCT/US2013/055196 on Aug. 15, 2013, now abandoned.
(Continued)

(51) Int. Cl.
*A61B 5/05* (2021.01)
*A61M 25/01* (2006.01)
(Continued)

(52) U.S. Cl.
CPC ......... *A61M 25/0127* (2013.01); *A61B 5/055* (2013.01); *A61B 18/04* (2013.01); *A61L 29/06* (2013.01); *A61L 29/18* (2013.01); *A61M 25/0082* (2013.01); *A61N 7/022* (2013.01); *G01R 33/287* (2013.01); *G01R 33/4814* (2013.01); *A61B 8/429* (2013.01);
(Continued)

(58) Field of Classification Search
CPC .......... A61M 25/0127; A61M 25/0082; A61B 5/055; A61B 18/04
See application file for complete search history.

(56) References Cited

U.S. PATENT DOCUMENTS

| 4,276,779 A | 7/1981 | Davis, Jr. |
| 4,326,529 A | 4/1982 | Doss et al. |

(Continued)

FOREIGN PATENT DOCUMENTS

EP    2 455 133 A1    5/2012

OTHER PUBLICATIONS

Chopra et al., "MRI-compatible transurethral ultrasound system for the treatment of localized prostate cancer using rotational control", Medical Physics, vol. 35, No. 4, pp. 1346-1357, Apr. 2008.
(Continued)

*Primary Examiner* — Joel F Brutus
(74) *Attorney, Agent, or Firm* — Foley & Lardner LLP

(57) ABSTRACT

A magnetic resonance compatible catheter. The catheter incorporates directional high intensity ultrasound. The catheter may include imaging coils visible through magnetic resonance imaging. The location and placement of the catheter may be controlled by steering wires within lumen in the catheter guided by the location information from the magnetic resonance imaging.

19 Claims, 28 Drawing Sheets

Related U.S. Application Data

(60) Provisional application No. 61/683,557, filed on Aug. 15, 2012.

(51) Int. Cl.

| | | |
|---|---|---|
| *A61B 5/055* | (2006.01) | |
| *A61N 7/02* | (2006.01) | |
| *G01R 33/48* | (2006.01) | |
| *A61L 29/18* | (2006.01) | |
| *A61L 29/06* | (2006.01) | |
| *A61B 18/04* | (2006.01) | |
| *A61M 25/00* | (2006.01) | |
| *G01R 33/28* | (2006.01) | |
| *A61B 18/00* | (2006.01) | |
| *A61B 17/00* | (2006.01) | |
| *A61B 8/00* | (2006.01) | |
| *A61B 90/00* | (2016.01) | |

(52) U.S. Cl.
 CPC ........... *A61B 2017/00323* (2013.01); *A61B 2018/00023* (2013.01); *A61B 2018/00166* (2013.01); *A61B 2018/00351* (2013.01); *A61B 2018/00547* (2013.01); *A61B 2018/00577* (2013.01); *A61B 2018/00791* (2013.01); *A61B 2090/064* (2016.02); *A61B 2090/374* (2016.02); *A61B 2090/3954* (2016.02); *A61B 2562/164* (2013.01); *A61M 2025/0166* (2013.01)

(56) References Cited

U.S. PATENT DOCUMENTS

| | | | |
|---|---|---|---|
| 4,976,709 A | | 12/1990 | Sand |
| 5,057,104 A | | 10/1991 | Chess |
| 5,143,063 A | | 9/1992 | Fellner |
| 5,391,197 A | | 2/1995 | Burdette et al. |
| 5,456,259 A | * | 10/1995 | Barlow ............... A61B 8/4488 |
| | | | 600/459 |
| 5,458,585 A | * | 10/1995 | Salmon ................ A61B 8/445 |
| | | | 600/467 |
| 5,471,988 A | | 12/1995 | Fujio et al. |
| 5,522,869 A | | 6/1996 | Burdette et al. |
| 5,533,401 A | | 7/1996 | Gilmore |
| 5,549,638 A | | 8/1996 | Burdette |
| 5,620,479 A | | 4/1997 | Diederich |
| 5,810,801 A | | 9/1998 | Anderson et al. |
| 5,849,029 A | | 12/1998 | Eckhouse et al. |
| 5,964,749 A | | 10/1999 | Eckhouse et al. |
| 6,049,159 A | | 4/2000 | Barthe et al. |
| 6,050,943 A | | 4/2000 | Slayton et al. |
| 6,113,559 A | | 9/2000 | Klopotek |
| 6,254,553 B1 | | 7/2001 | Lidgren et al. |
| 6,258,086 B1 | | 7/2001 | Ashley et al. |
| 6,325,769 B1 | | 12/2001 | Klopotek |
| 6,350,262 B1 | | 2/2002 | Ashley |
| 6,350,276 B1 | | 2/2002 | Knowlton |
| 6,377,854 B1 | | 4/2002 | Knowlton |
| 6,377,855 B1 | | 4/2002 | Knowlton |
| 6,381,497 B1 | | 4/2002 | Knowlton |
| 6,381,498 B1 | | 4/2002 | Knowlton |
| 6,387,380 B1 | | 5/2002 | Knowlton |
| 6,394,956 B1 | | 5/2002 | Chandrasekaran et al. |
| 6,405,090 B1 | | 6/2002 | Knowlton |
| 6,413,255 B1 | | 7/2002 | Stern |
| 6,425,912 B1 | | 7/2002 | Knowlton |
| 6,430,446 B1 | | 8/2002 | Knowlton |
| 6,438,424 B1 | | 8/2002 | Knowlton |
| 6,461,378 B1 | | 10/2002 | Knowlton |
| 6,470,216 B1 | | 10/2002 | Knowlton |
| 6,575,969 B1 | | 6/2003 | Rittman et al. |
| 6,595,934 B1 | | 7/2003 | Hissong et al. |
| 6,626,902 B1 | * | 9/2003 | Kucharczyk ....... A61B 5/14539 |
| | | | 606/41 |
| 6,673,063 B2 | | 1/2004 | Brett |
| 6,726,684 B1 | | 4/2004 | Woloszko et al. |
| 6,929,640 B1 | | 8/2005 | Underwood et al. |
| 6,980,862 B2 | | 12/2005 | Fredricks et al. |
| 7,270,658 B2 | | 9/2007 | Woloszko et al. |
| 7,331,956 B2 | | 2/2008 | Hovda et al. |
| 7,462,178 B2 | | 12/2008 | Woloszko et al. |
| 7,473,224 B2 | | 1/2009 | Makin |
| 7,806,892 B2 | | 10/2010 | Makin et al. |
| 8,292,815 B2 | | 10/2012 | Burdette et al. |
| 8,790,281 B2 | | 7/2014 | Diederich et al. |
| 9,119,954 B2 | | 9/2015 | Burdette et al. |
| 2001/0003791 A1 | | 6/2001 | Burbank et al. |
| 2001/0031922 A1 | | 10/2001 | Weng et al. |
| 2002/0016546 A1 | | 2/2002 | Cerofolini |
| 2002/0035361 A1 | | 3/2002 | Houser et al. |
| 2002/0068869 A1 | | 6/2002 | Brisken et al. |
| 2002/0087081 A1 | * | 7/2002 | Serrano ................ A61B 8/12 |
| | | | 600/459 |
| 2002/0095144 A1 | | 7/2002 | Carl |
| 2002/0151940 A1 | | 10/2002 | Bar-Cohen et al. |
| 2003/0013960 A1 | | 1/2003 | Makin et al. |
| 2003/0014093 A1 | | 1/2003 | Makin |
| 2003/0032898 A1 | | 2/2003 | Makin et al. |
| 2003/0069569 A1 | | 4/2003 | Burdette et al. |
| 2003/0130598 A1 | | 7/2003 | Manning et al. |
| 2003/0163067 A1 | | 8/2003 | Lidgren |
| 2003/0216721 A1 | * | 11/2003 | Diederich ............. A61N 7/02 |
| | | | 607/96 |
| 2005/0015024 A1 | | 1/2005 | Babaev |
| 2005/0036976 A1 | | 2/2005 | Rubin et al. |
| 2005/0090816 A1 | | 4/2005 | McClurken et al. |
| 2005/0228318 A1 | | 10/2005 | Iger |
| 2005/0234343 A1 | | 10/2005 | Maschke |
| 2005/0261584 A1 | | 11/2005 | Eshel et al. |
| 2006/0074314 A1 | | 4/2006 | Slayton et al. |
| 2006/0074355 A1 | | 4/2006 | Slayton et al. |
| 2006/0206105 A1 | | 9/2006 | Chopra et al. |
| 2006/0241436 A1 | | 10/2006 | Sunnanvader |
| 2006/0264747 A1 | | 11/2006 | Freeman et al. |
| 2007/0016062 A1 | | 1/2007 | Park et al. |
| 2007/0088244 A1 | | 4/2007 | Miller et al. |
| 2007/0203555 A1 | * | 8/2007 | Williams ......... A61M 25/0041 |
| | | | 607/122 |
| 2007/0255267 A1 | | 11/2007 | Diederich et al. |
| 2008/0004614 A1 | | 1/2008 | Burdette et al. |
| 2008/0039746 A1 | | 2/2008 | Hissong et al. |
| 2008/0125674 A1 | * | 5/2008 | Bilecen ................ A61B 31/06 |
| | | | 600/585 |
| 2009/0018446 A1 | * | 1/2009 | Medan ................ A61N 7/022 |
| | | | 600/439 |
| 2009/0292199 A1 | * | 11/2009 | Bielewicz ............. A61B 8/445 |
| | | | 600/459 |
| 2010/0049186 A1 | | 2/2010 | Ingle et al. |
| 2010/0312095 A1 | * | 12/2010 | Jenkins ................ A61B 5/415 |
| | | | 600/411 |
| 2010/0312096 A1 | * | 12/2010 | Guttman ............... A61B 34/25 |
| | | | 600/411 |
| 2016/0008635 A1 | | 1/2016 | Burdette et al. |
| 2016/0030773 A1 | | 2/2016 | Burdette |

OTHER PUBLICATIONS

Diederich et al., "Catheter-Based Ultrasound Devices and MR Thermal Monitoring for Conformal Prostate Thermal Therapy", 30th Annual International IEEE EMBS Conference Vancouver, British Columbia, Canada, Aug. 20-24, 2008, pp. 3664-3668.

Diederich et al., "An Improved Bolus Configuration for Commercial Multielement Ultrasound and Microwave Hyperthermia Systems", Med. Phys. 21(9), Sep. 1994, pp. 1401-1403, Am. Assoc. Phys. Med.

Diederich et al., "Transurethral Ultrasound Applicators with Directional Heating Patterns for Prostate Thermal Therapy: In Vivo Evaluation Using Magnetic Resonance Thermometry", Med. Phys. 31(2), Feb. 2004, pp. 1-9, Am. Assoc. Phys. Med.

Diederich, C.J., et al., "Ultrasound Technology for Hyperthermia", Ultrasound in Med. & Biol., Mar. 26, 1999, 25(6):871-887.

(56) References Cited

OTHER PUBLICATIONS

El-Desouki, M. M., et al., "Driving Circuitry for Focused Ultrasound Noninvasive Surgery and Drug Delivery Applications", Sensors, Jan. 7, 2011, 11:539-556.

Hynynen, K., et al., "Image-guided ultrasound phased arrays are a disruptive technology for non-invasive therapy", Phys. Med. Biol., Aug. 5, 2016, 61:R206-R248, and corrigendum, 2018.

Prakash, et al., Patient Specific Optimization-Based Treatment Planning for Catheter-Based Ultrasound Hyperthermia and Thermal Ablation, Proceedings of SPIE, vol. 7181 71810E, 2009, 10 pages.

Prionas et al., Temperature Distributions Induced in Pig Tissues by a Water-Cooled Disk Electrode rf System, Med. Phys. 11(1), Jan./Feb. 1984, pp. 22-25, Am. Assoc. Phys. Med.

Ross et al., "Highly directional transurethral ultrasound applicators with rotational control for MRI-guided prostatic thermal therapy", Physics in Medicine and Biology, Jan. 21, 2004, 49(2):189-204.

U.S. Office Action for U.S. Appl. No. 10/230,949, dated Mar. 22, 2006, 6 pages.

U.S. Office Action for U.S. Appl. No. 11/818,046, dated Jul. 23, 2009, 7 pages.

U.S. Office Action for U.S. Appl. No. 12/004,753, dated Sep. 25, 2009, 7 pages.

U.S. Office Action for U.S. Appl. No. 11/744,773, dated Mar. 5, 2010, 8 pages.

U.S. Office Action for U.S. Appl. No. 12/004,753, dated Apr. 12, 2010, 7 pages.

U.S. Office Action for U.S. Appl. No. 11/818,046, dated Apr. 14, 2010, 11 pages.

U.S. Office Action for U.S. Appl. No. 11/744,773, dated Nov. 12, 2010, 10 pages.

U.S. Office Action for U.S. Appl. No. 11/818,046, dated Dec. 28, 2010, 8 pages.

U.S. Office Action for U.S. Appl. No. 11/818,046, dated Oct. 5, 2011, 9 pages.

European Office Action for EPO Application 08745765.1, dated Jan. 23, 2013, 5 pages.

U.S. Office Action for U.S. Appl. No. 11/744,773, dated Oct. 11, 2013, 12 pages.

International Search Report and Written Opinion for Application No. PCT/US52013/055196, dated Nov. 12, 2013, 13 pages.

U.S. Office Action for U.S. Appl. No. 13/657,464, dated Mar. 13, 2014, 13 pages.

U.S. Office Action for U.S. Appl. No. 11/744,773, dated Apr. 2, 2014, 10 pages.

International Search Report and Written Opinion in PCT/US2014/014728, dated Jun. 5, 2014, 6 pages.

International Search Report and Written Opinion in PCT/US2014/024938, dated Aug. 21, 2014, 7 pages.

U.S. Office Action for U.S. Appl. No. 13/657,464, dated Sep. 29, 2014, 14 pages.

U.S. Office Action for U.S. Appl. No. 11/744,773, dated Dec. 12, 2014, 10 pages.

International Preliminary Report on Patentability for PCT Application No. PCT/US2013/055196, dated Feb. 17, 2015, 7 pages.

U.S. Office Action for U.S. Appl. No. 11/744,773, dated Jul. 10, 2015, 11 pages.

U.S. Office Action for U.S. Appl. No. 11/744,773, dated Mar. 11, 2016, 16 pages.

U.S. Office Action for U.S. Appl. No. 14/841,586, dated Apr. 8, 2016, 17 pages.

Office Action for U.S. Appl. No. 11/744,773, dated Aug. 11, 2016, 13 pages.

Final Office Action in U.S. Appl. No. 14/841,286, dated Oct. 14, 2016, 12 pages.

Final Office Action in U.S. Appl. No. 11/744,773, dated Feb. 27, 2017, 16 pages.

Office Action in U.S. Appl. No. 14/841,586, dated Aug. 4, 2017, 12 pages.

Final Office Action in U.S. Appl. No. 11/744,773, dated Aug. 10, 2017, 18 pages.

Non-Final Office Action on U.S. Appl. No. 16/252,481, dated Nov. 17, 2020, 11 pages.

* cited by examiner

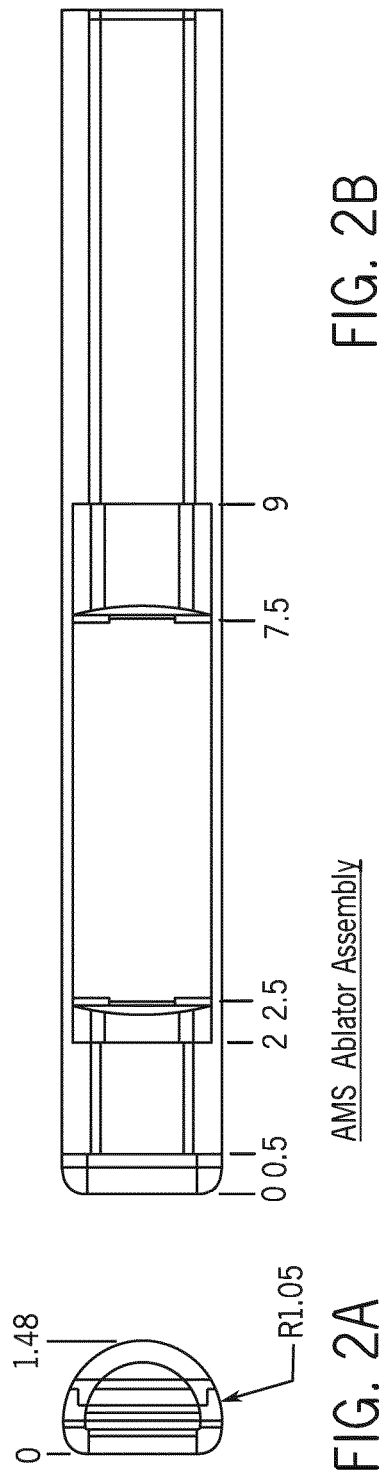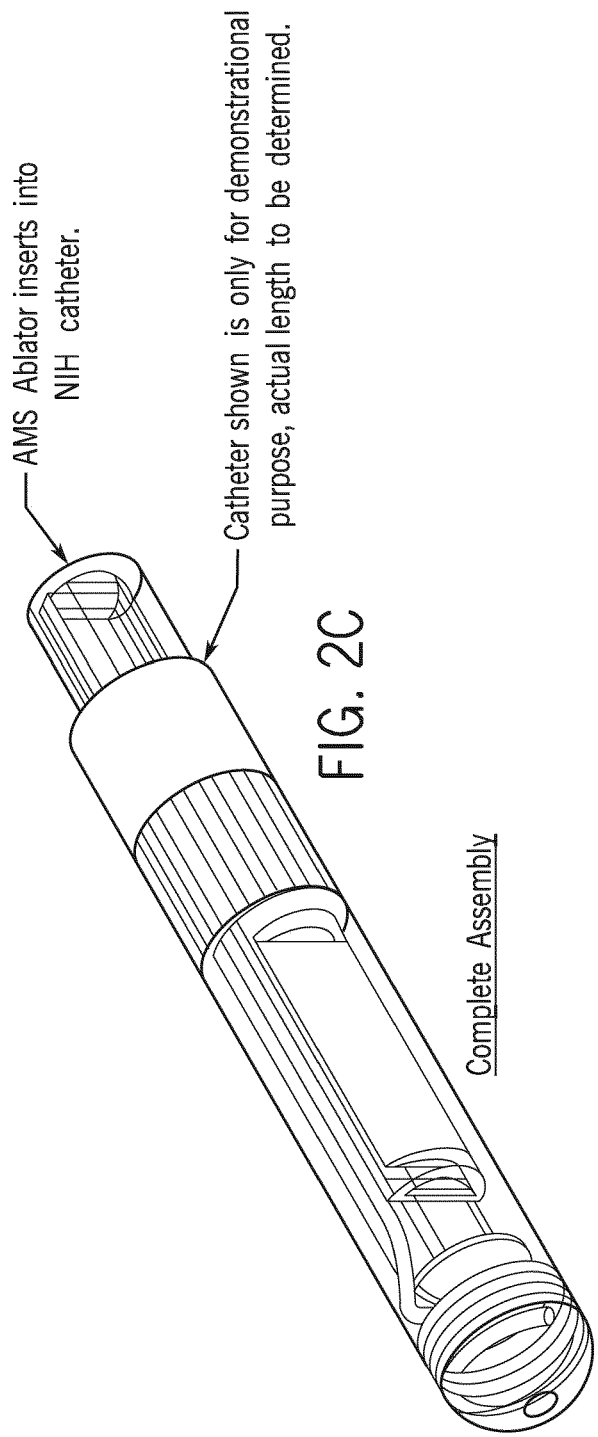

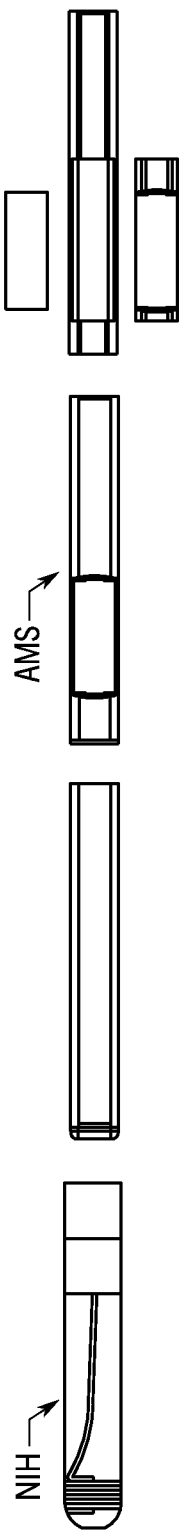
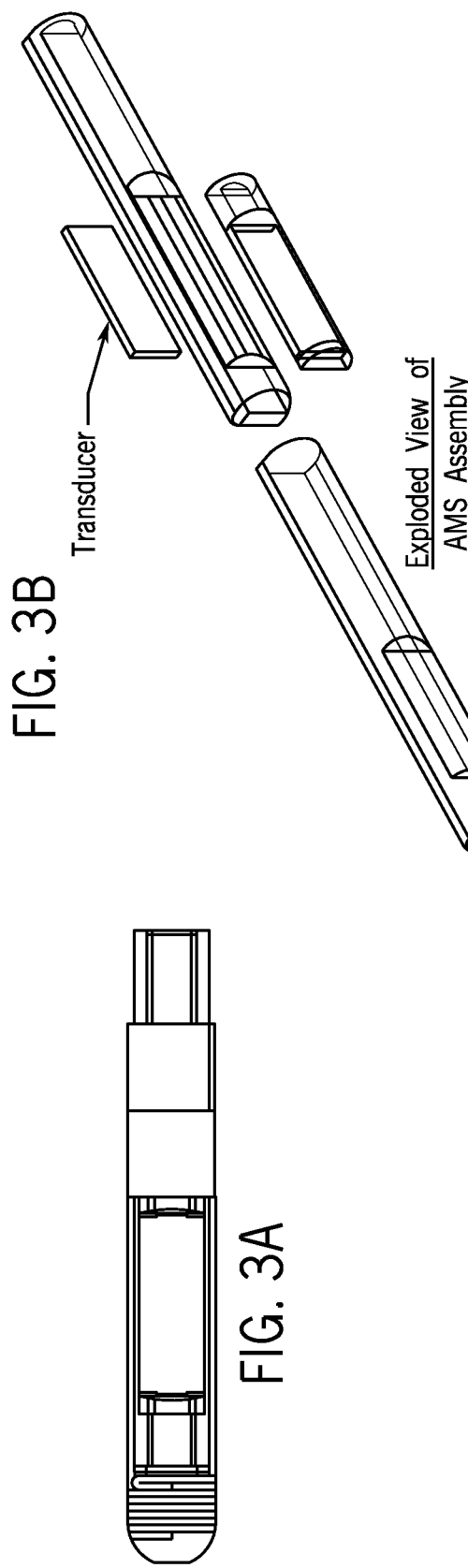

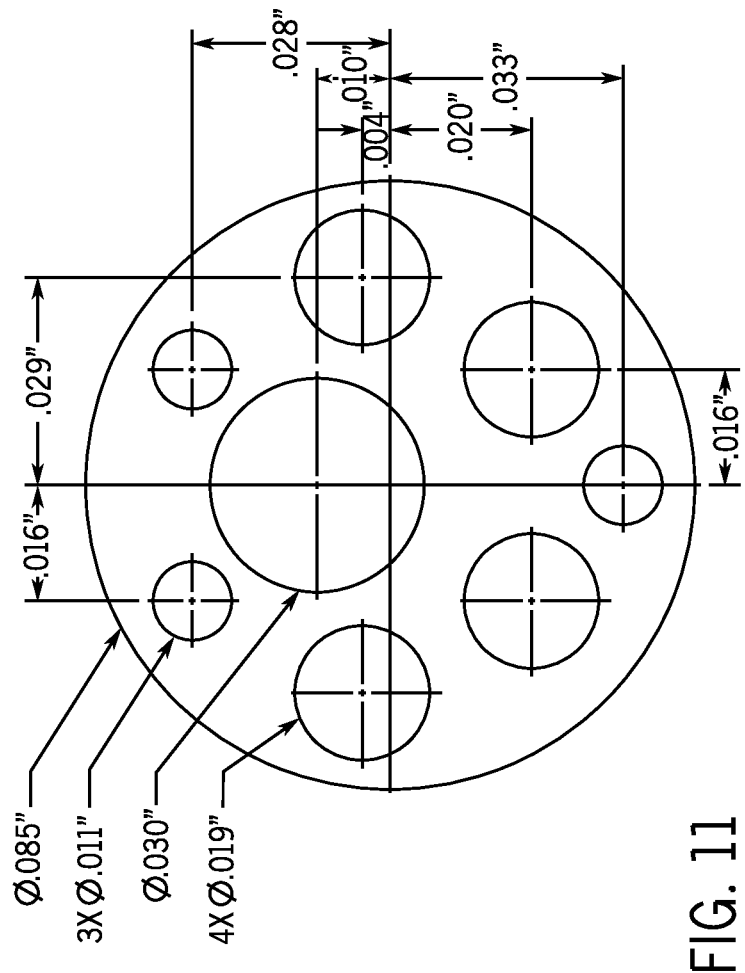
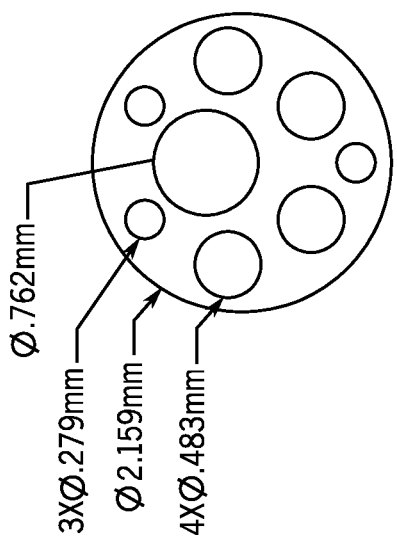
FIG. 11
*Note: Cut to 95cm length

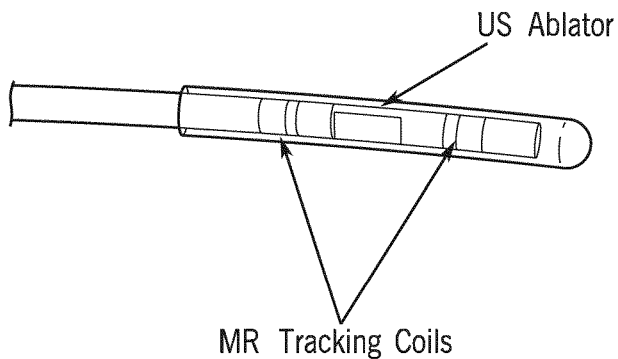
FIG. 14A
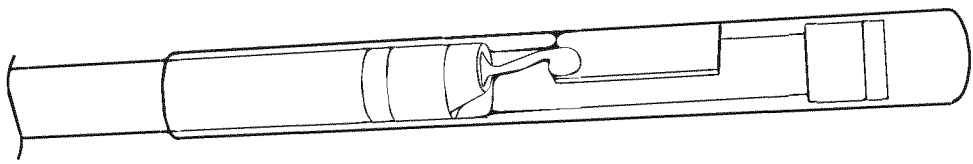
FIG. 14B
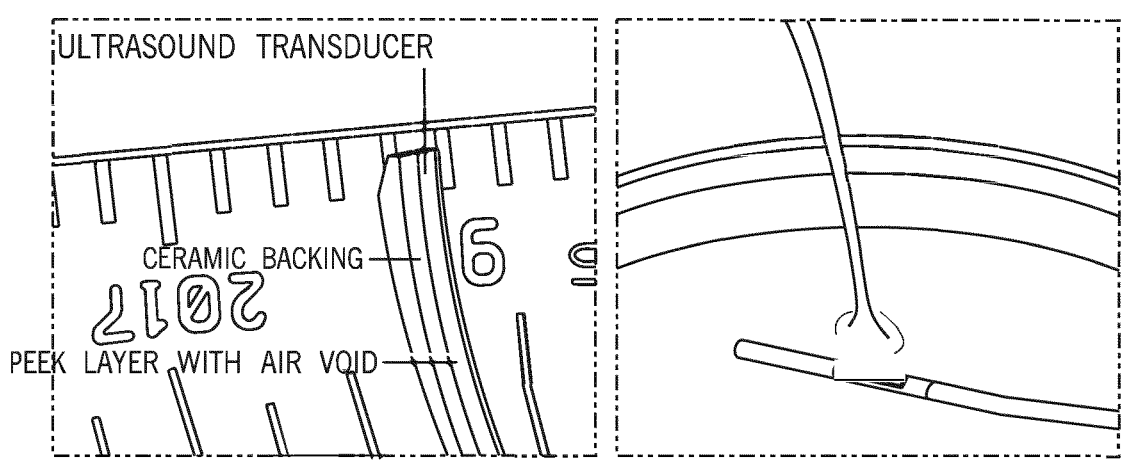
FIG. 14C
FIG. 14D

Directional Applicator Transducer Muscle Tissue

Positioning of Ablator. Temperature Probes at 5 MM and 9 MM from transducer.
Treatment is toward top and needle inserted from right to left as viewed.

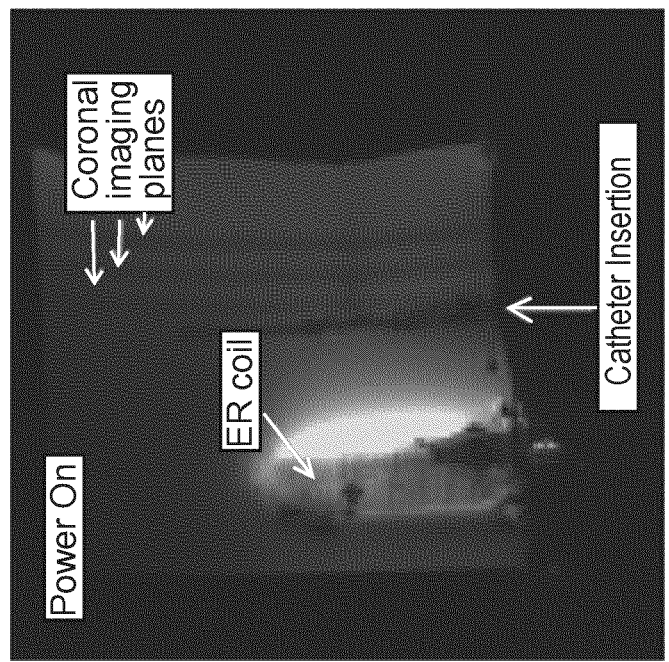
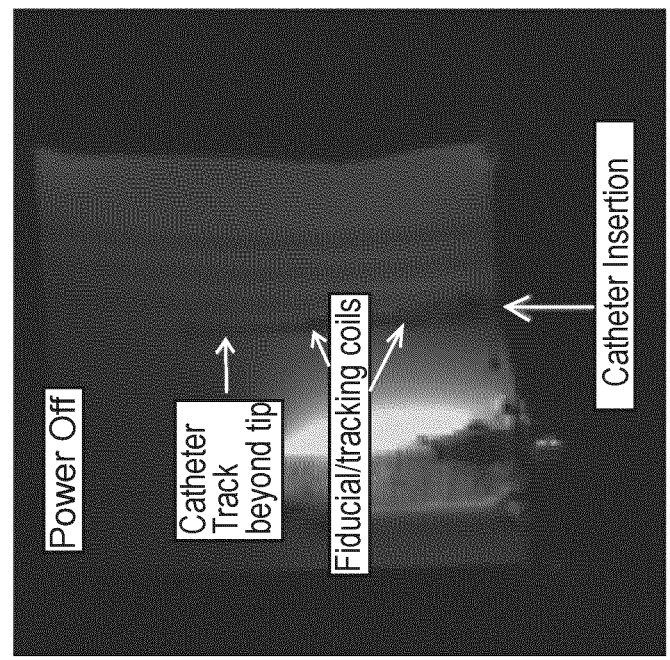
FIG. 27

MRI COMPATIBLE ABLATION CATHETER SYSTEM INCORPORATING DIRECTIONAL HIGH-INTENSITY ULTRASOUND FOR TREATMENT

CROSS-REFERENCE TO RELATED PATENT APPLICATIONS

This application is a continuation of U.S. patent application Ser. No. 14/421,902, filed Feb. 16, 2015, which is the U.S. National Phase application of PCT/US2013/055196, filed Aug. 15, 2013, which claims priority from U.S. Provisional Application 61/683,557, filed Aug. 15, 2012, all of which are incorporated herein by reference in their entirety.

BACKGROUND OF THE INVENTION

Over the past 30 years, several different types of heating technology have been developed for minimally invasive thermal therapy including lasers, radiofrequency (RF), microwaves (MW), and conduction or cautery sources, as well as cryotherapy for freezing. Regardless of the technology employed, the primary challenge in utilizing thermal therapy is to selectively treat the targeted tissue without damaging the surrounding healthy tissue. Unfortunately, all of the aforementioned technologies have inherent limited ability to efficiently deliver target conformed energy to a volume of tissue, as well as inherent limited ability to control or shape the energy output and heating of that tissue. Control of the thermal damage is primarily limited to the applied power level and the duration of heating. Such devices essentially produce a small "hot spot" (or "iceball," for cryotherapy) that diffuses outward by thermal conduction—a process that is uncontrolled due to the heterogeneous and dynamic properties of the tissue and perfusion thereof.

Therapeutic ultrasound has the potential to eliminate all of these problems due to its fundamental characteristics at useful therapeutic frequencies which both penetrate tissue effectively and can be readily focused or directive. Ultrasound provides the unique ability to dynamically control and direct the heating of target tissue volume—the key difference between AMS (Acoustic MedSystems) technology and other thermal devices. This is possible because of the fundamental physical nature of ultrasound propagation, penetration, and attenuation in cardiac muscle tissue. At the frequencies used for thermal treatment (approximately 5-12 MHz), the wavelength of the ultrasound in tissue is much less than 1 millimeter, allowing for precise targeting of the acoustic energy beam, similar to optical directivity and precision. Just as important, the high-power ultrasound energy actually penetrates and directly propagates into the tissue. Rather than heat transfer simply by thermal conduction, the ultrasound energy is transmitted directly into the target tissue to rapidly produce highly controlled volumes of thermal necrosis. The ultrasound-emitting transducer elements are fabricated to form custom shapes and collimated acoustic beams, providing three-dimensional, directional control of the ultrasound energy output. This control results in the ability to effectively target and thermally coagulate or ablate a specific region of tissue conforming to the target while safely preserving the surrounding healthy tissue.

Further, there are certain types of diseases and conditions for which an improved treatment methodology is needed. For example, atrial fibrillation is the most common type of serious arrhythmia. It involves a very fast and irregular contraction of the atria. In AF, the heart's electrical signals don't begin in the SA node. Instead, they begin in another part of the atria or in the OS of the pulmonary veins. This increases risk of stroke and heart failure. Paroxysmal Supraventricular Tachycardia (PSVT) is a serious arrhythmia where the conduction pathways between atria and ventricles exhibit re-entrant pathways. Wolff-Parkinson-White (WPW) syndrome is a more serious type of PSVT with an extra conduction pathway from the atria to the ventricles. Antiarrhythmic drugs such as beta blockers, digitalis, and calcium channel blockers can be used to slow down or make the heart beat more regular. Other antiarrhythmic drugs can be applied to control heart rhythm, but in some cases increase arrhythmia or generate a different kind of arrhythmia. In a significant number of cases drugs do not effectively control the arrhythmia, or generate complications, or are not tolerated. Additionally, many types of arrhythmia are best treated upfront with catheter ablation, including ventricular fibrillation.

SUMMARY OF THE INVENTION

One implementation relates to an apparatus for treating tissue with ultrasound. The apparatus comprises a catheter having an outer tube. The apparatus further includes an ultrasonic transducer positioned on a rigid platform, the rigid platform disposed within the catheter and a plurality of lumens.

Another implementation relates to a system for magnetic resonance imaging compatible ablative treatment of a target site. The system includes a catheter having an outer tube, at least one imaging coil, an ultrasonic transducer positioned on a rigid platform, the rigid platform disposed within the catheter, and a first inner tube and a second inner tube. The system further includes a magnetic imaging system capable of detecting the at least one imaging coil. The system also includes a 3-dimensional modeling and guidance system having a 3-dimensional model of the target site and in communication with the magnetic imaging system to provide an indication of the position of the catheter with respect to the target site.

Another implementation relates to a method for ablating target cardiac. A catheter having an ultrasonic transducer is positioned in proximity to a target tissue. A position of the catheter is determined using magnetic resonance imaging. The catheter, based upon the determined position, is guided to a treatment zone of the target tissue. The tissue is treated with ultrasonic energy.

Additional features, advantages, and embodiments of the present disclosure may be set forth from consideration of the following detailed description, drawings, and claims. Moreover, it is to be understood that both the foregoing summary of the present disclosure and the following detailed description are exemplary and intended to provide further explanation without further limiting the scope of the present disclosure claimed.

BRIEF DESCRIPTION OF THE DRAWINGS

The foregoing and other objects, aspects, features, and advantages of the disclosure will become more apparent and better understood by referring to the following description taken in conjunction with the accompanying drawings, in which:

FIGS. 2A-2C is a second design approach incorporating an inner ultrasound ablation catheter with single tracking coil that is intended to be concentric with an outer placement catheter that would include the steering guidewires and a second tracking coil.

FIGS. 3A-3C is an exploded view of the dual concentric catheter approach detailing the AMS ultrasound ablator portion of the inner catheter.

FIG. 11 is a cross-sectional view of custom extruded ablation catheter design. Each of the holes are labeled as to their use and dimensioned.

FIGS. 14A-14D is a final ultrasonic ablation catheter with integrated steering guide wires, MR tracking coils, power delivery, and water circulation: (14A) note greater spacing between tracking coils and ablation transducer; (14B) note closer spacing between coils and ablator element and shorter distal tip; 14C Details of the ceramic backing to improve durability of the transducer assembly. 14D High-Intensity ultrasound power on and streaming fountain from water surface to demonstrate amount of energy and acoustic pressure obtained indicative of high efficiency of device.

FIG. 27 has MRI magnitude images of applicator within phantom before and during power on, showing negligible difference which indicates RF noise with the system and device is not significant.

DETAILED DESCRIPTION OF THE PREFERRED EMBODIMENTS

Figure 1A:
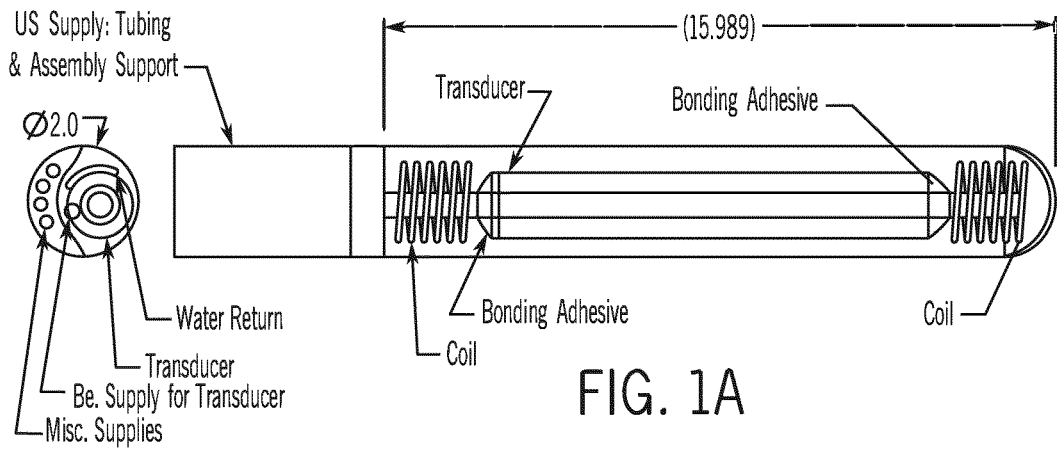
FIGS. 1A-1C is an example of design drawing and initial concepts evaluated with empirical development and testing. The catheter incorporates a single transducer element. The catheter is 2.3 mm diameter and the diameter at the balloon is 3.15 mm, not inflated, 3.3 mm inflated.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

Based upon extensive experimentation, as well as substantial experience with other thermal devices, implementations of the invention offer the control and performance to overcome the shortcomings of existing thermal devices and provide physicians and their patients with optimum clinical results. This system in conjunction with new Magnetic Resonance ("MR") or Magnet Resonance Imaging ("MRI") guided tracking technology can provide guidance of the therapy catheter insertion, anatomical imaging, and real-time monitoring and feedback of the treatment process. Furthermore, this integrated system provides advanced software for pre-treatment planning as well as post-treatment evaluation to ensure the effectiveness of the thermal therapy. The ultrasound ablation technology for minimally invasive thermal therapy, in combination with real-time image guidance and visualization, work together to significantly improve the ability for selective targeting of tissue. Other example applications for use of image guided minimally invasive therapy are treatment of brain tumors under MRI guidance, treatment of prostate disease under MRI or ultrasound image guidance, treatment of liver cancer and kidney tumors using image guidance and with or without 3D spatial tracking as performed by the inventors and others. Additionally, high intensity focused ultrasound is used under ultrasound guidance for treatment of uterine fibroids and breast. The inventors have also used minimally invasive ultrasound needles placed under ultrasound image guidance and also with fluoroscopic-CT image guidance for treating metastatic spine tumors.

In one implementation, such system and methods may be used to treat cardiac conditions, such as cardiac rhythm disorders via transarterial, endovenous, transseptal atrial, and transaortic endoventricular access requires a highly flexible device with precise control of directivity and volume of ablation. Inherent technical difficulties in existing ablation systems have limited the efficacy and application of ablation procedures, namely, 1) lack of adequate image guidance and 2) poor control of the size/shape of ablation zone. Development of devices for controlled highly conformable ablative thermal therapy for treatment of cardiac rhythm disorders via flexible intraluminal delivery catheters could have a highly significant impact on this disease. Thus, one implementation provides devices and methods for accurate, conformal treatment of cardiac arrhythmias under MR guidance using steerable catheter-based ultrasound devices which incorporate tracking coils for active tip localization and registration. This catheter-based ultrasound device has potential to actively shape and control ablation, under real-time monitoring using spatially-registered MR thermal imaging (MRTI) and MRI localization. The controllability and fast penetration of the ultrasound heating energy from these catheters has the potential to provide a significant improvement over existing radiofrequency (RF) devices as typically applied for minimally invasive ablation of arrhythmias, which are limited to fixed ablation profiles, low therapy penetration distance, requirement of multiple placements, and not MR compatible (artifacts). Furthermore, MRI and MR temperature imaging is becoming established as an accurate method for targeting and directing thermal therapy in many other applications including localized cancers and uterine fibroids. As noted below, through design of unique MR compatible high-frequency small catheter ultrasound ablators and supporting systems, the ability to deliver substantial energy to tissue to produce controlled lesions while under MR guidance and temperature monitoring has been demonstrated.

One implementation relates to flexible ultrasound ablators. As noted below, implementations of such ablators have been demonstrated to be used to deliver highly conformable and controllable volume thermal ablative therapies under MRI guidance and control. This MRI-guided ultrasound technology appears feasible to enable novel approaches to therapy for cardiac rhythm disorders.

In one particular implementation of an abalator, the device is an ultrasound ablation probe designed specifically for introduction via an intraluminal device which is suitable for tracking using MRI. The focus of this effort is the primary application of MRI-guided catheter-based ablation of myocardium from inside the heart for the purpose of treating heart rhythm disorders. Other treatment applications of ultrasound ablators encompass disease sites such as liver, kidney, prostate, pancreas, lung, brain, spine, bladder, colorectal and cervix. Interventional image guidance, high-intensity ultrasound ablation technology, treatment planning/dose optimization, and clinical systems integration are combined to develop minimally invasive devices and integrated systems. The specific products are ablation treatment planning, guidance software and systems, and high intensity needle-based and catheter-based interventional devices for thermal ablative therapy. These devices create minimally invasive tracked guidance systems to deliver highly conformal (shape, volume) controlled high-intensity ultrasound energy delivery for customized disease treatment.

As described below, the ablator was utilized in the treatment of cardiac rhythm disorders (arrhythmias). The treatment was of the Left ventricle and there were two approaches: an Endocavity approach and an approach from Right atrium across septum into left atrium and then into left ventricle from aortic valve. The goal of the treatment was to ablate a portion of ventricular wall under MR guidance. The procedure included positioning over the ablation target;

confirming treatment zone; and treating the target. The depth of treatment: controllable 0-15 mm. Frequency and power level are important to control of treatment depth. Modeling is very useful in designing treatment delivery parameters. Most suitable frequency range for cardiac ablation applications are 5-12 MHz. US ablator drive power from 5-25 watts per active element is sufficient for these cardiac applications. Variable longitudinal treatment length along catheter at tip (3-8 mm); desired is 5 mm length as baseline starting lesion length.

For transmural lesions made along the left ventricle, the catheter would be alongside and in contact with the myocardium. It would follow the curvature of the ventricular myocardium to maintain contact, particularly at the region where the US ablation would be delivered in a "sidefire" fashion.

There is a need to visualize the catheter shape and tip at all times. Two MR imaging coils will be incorporated along the catheter length. One coil needs to be at the distal tip of the catheter, the other proximal to the US ablator.

In one implementation, a multi-lumen catheter approach is utilized. Ablation zone is "sidefire", about 5 mm length (devices made with lengths varying from 3 mm to 15 mm with excellent control and performance) and controllable depth into the ventricular cardiac muscle. A lumen within the overall MRI guided ablation catheter wherein an US ablator is inserted is one implementation. Another implementation is incorporation of the US ablator transducer configuration near the distal end of a multi-lumen catheter and use appropriate channels for wiring of the transducer configuration for power. Thus, the lumen (working channel) for the AMS US ablator must be eccentric to the center of the overall MR guidance catheter. The smaller working channels will carry the MR coil leads and any steering guide wires used.

In one implementation, the total MR catheter length will be 90 cm working length, not including connectors, etc. In one implementation, the desired bend radius of the catheter (and the US ablator) is 2 cm. A bend radius of 4 cm would be the greatest tolerable.

In one implementation, the catheter device includes integration of RF tracking coils, RF pacing, steering & positioning, high-powered ultrasonic transducers to enable real-time image-guided cardiac interventions.

In one implementation, 3D modeling is employed for optimizing device design and development of treatment delivery with control strategies. Anatomy specific 3D bio-acoustic models can be used for a particular application, such as cardiac tissue, and incorporate catheter ultrasound devices, dynamic tissue properties, and convective cooling.

In one implementation, a system is provided for use with a catheter, the system comprising one or more of a RF amplifier, power supply, electrical isolation, catheter cooling, controller, and monitoring can be incorporated. The system allows operation within MR suite w/access through room penetration panel and, appropriate RF filtering and isolation included, and parallel integration with multi-slice tracking and monitoring software. The amplifier may be a low harmonic distortion, compact, low noise, and high efficiency design. A closed loop flow system for acoustic coupling and US ablator transducer cooling may be sued.

In one implementation, the system integrates MRI techniques for active tracking localization and MR temperature imaging in support of real-time guidance of ultrasonic cardiac ablation. Use of small MR contrast markers integrated into the US ablation catheter at a minimum of two locations enables accurate rotational control of catheter position. The combination of coils and markers enables 3D localization and energy directional control and application with respect to the target tissue. Real time control includes, in one implementation, application of pulse sequences for real-time tracking, incorporation of multi-slice imaging with fast re-alignment, and MR temperature monitoring with multi-baseline PRF. An important aspect of performing an MR-guided interventional procedure is the availability of good visualization and display software for targeting and monitoring the treatment. One implementation utilizes RTHawk® (HeartVista), which is an imaging platform developed for cardiac and interventional applications that allows image acquisition and MR parameter adjustment in real-time.

An important aspect of performing an MR-guided interventional procedure is the availability of good visualization and display software for targeting and monitoring the treatment. RTHawk (HeartVista) is an imaging platform developed for cardiac and interventional applications that allows image acquisition and MR parameter adjustment in real-time. We will use existing RTHawk features and integrate additional features to allow procedure guidance and monitoring specific to ultrasonic catheter ablation of cardiac targets.

MR-guidance will be used to track the catheter position and automatically localize the scan plane through the device. MR tracking based upon micro-coils on the device to provide a localized signal source, which is then tracked in real time. For certain implementations, the system includes fast tracking capabilities to the MR monitoring environment to exploit the micro-coils integrated into the ultrasound catheter. Once the position of the tracking coil is known, a new slice through the catheter is automatically prescribed for the next image acquisition. A major challenge in locating the microcoil is that the quality of the detected MR signal can be degraded by undesired MR signals that are coupled into the microcoil. In addition, measured microcoil location can also be shifted by magnetic field offsets caused by magnetic susceptibility gradients if the microcoil/catheter is not well matched to its surroundings. Implementations can implement MR-tracking sequences for both Hadamard and zero-phase reference multiplexing approaches. In one implementation, a phase dithering strategy is utilized to increase the robustness of active MR tracking. The implementation uses dephasing magnetic field gradient pulses that are applied orthogonal to the frequency encoding gradient axis and rotated about it in subsequent acquisitions. Since the desired signal comes from a small volume near the microcoil, the signal is not dramatically altered by the dephasing gradient. Undesired signals arising from larger areas, e.g. due to coupling from other coils, are dephased and reduced in signal intensity. To obtain information about the catheter orientation two receive coils can be used or properties of the phase information introduced into the MR signal by a small receive coil can be exploited. In the latter case the phase information is directly related to the position and orientation of a small circular receive coil without the need of a 2nd coil.

In various implementations, the system allows for:
- MRI for tracking for targeting, and fast alignment of monitoring slices with device
- MRI temperature real-time localization and monitoring
- Fast lesion formation—larger and more contiguous volume, more consistent results
- Require fewer manipulations
- Lower maximum temps and no charring or explosive vaporization as commonly encountered with RF MRI for follow-up to ensure adequate and sustaining thermal lesion—irreversible Further, the materials and structure of the catheter can be selected to reduce the impact when used with MRI, for example anticipated catheter orientations, including rotation and deflection of distal catheter.

Real-time Temperature Sensitive MRI Pulse Sequence

Real-time temperature sensitive imaging sequences are utilized in one implementation to minimize intra-scan motion to provide good data for temperature reconstruction. There are a number imaging considerations that are unique to MR temperature imaging. First, real-time thermometry requires an image update rate that is higher than the change in temperature over time. So depending on the application, image update rates can vary quite substantially. For most applications that currently use MR temperature mapping, such as uterine fibroid or prostate ablation, image update times of about 10 sec are sufficient and tissue motion is of little concern. For the cardiac ablation proposed here, a gated and an ungated imaging strategy are believed to be feasible. In certain implementations, ablation times are up to one minute. An image update every 2-5 heartbeats is sufficient in such situations. If the ablation time is much shorter (<15-20 secs), update rates of more than one image in each heartbeat can be necessary and achieved within 1-5 seconds.

A second consideration in temperature imaging is the optimal spatial temperature resolution. For most thermal ablation applications, the temperature distribution varies slowly in space and does not have sharp edges as anatomical images do. If lower resolution can be used, the temperature measurements are more accurate, since the standard deviation in the temperature maps or temperature uncertainty is proportional to the inverse of the signal-to-noise ratio of the magnitude images. Another consideration is the imaging field of view (FOV). For temperature imaging of FUS ablation it is often not necessary to acquire a large FOV, since the heating spot will be confined to a small area. Therefore, techniques to decrease the FOV such as 2D excitation or saturation bands can be applied to increase temporal or spatial resolution.

Figure 34:
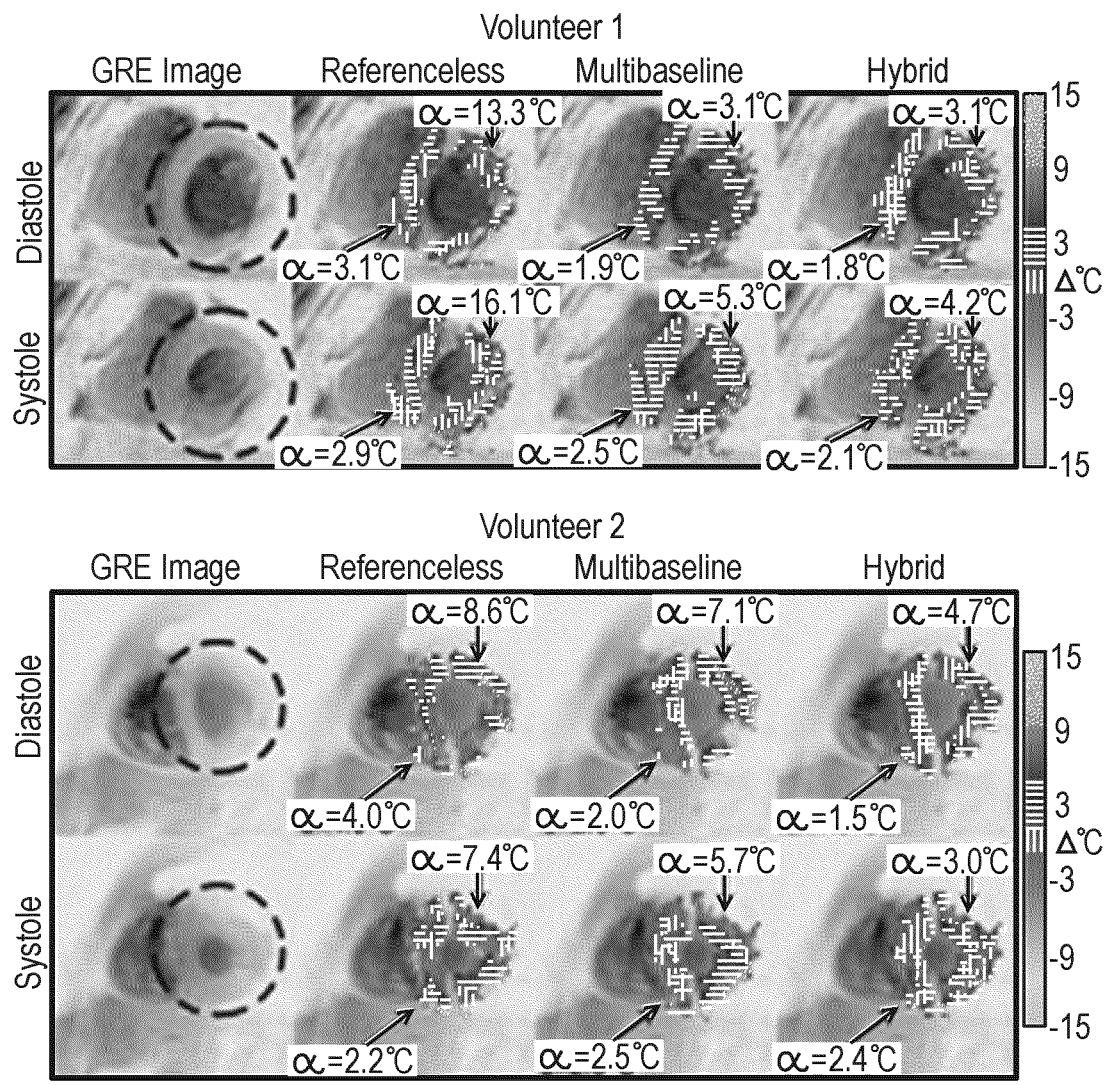
FIG. 34 has a comparison of temperature errors in the ventricular myocardium of human volunteers acquired with an interleaved spiral acquisition (single slice; 5 frames per second). The hybrid model has less artifacts than the other two methods. Standard deviations were calculated separately within the septum and LV free wall.

For long ablation times, it is sufficient to acquire an image (or few slices) within 2-5 heartbeats. For this case, a spoiled gradient-echo (GRE), ECG-gated CINE sequence with k-space segmentation can be implemented, where ½ of k-space lines are acquired in each heartbeat in combination with a flyback EPI or spiral readout. Instead of acquiring multiple cardiac phases, several slices will be obtained. For faster imaging as will be needed for short ablation, real-time cardiac imaging methods can be applied, such as single-shot or interleaved spirals or EPI. An example of temperature images acquired with an interleaved spiral sequence (single slice, 5 frames per second) is shown in FIG. 34. Acquisition time an can be sped up by using reduced FOV imaging and parallel imaging.

Temperature reconstruction with baseline subtraction is extremely sensitive to inter-frame motion. Even if the tissue motion is a simple translation such that the current image can be registered to the baseline image, changes in the background magnetic field will create temperature measurement errors. A hybrid referenceless and multi-baseline approach has been developed that greatly improves temperature measurements in the myocardium. Multibaseline methods work well when there is sufficient sampling of the background phase across the range of cardiac and respiratory motion. As shown in FIG. 34, there are errors when sampling is not sufficient. Referenceless methods are more flexible, but are ideally suited for larger, homogenous tissue areas. The proximity of the lungs and ribcage are difficult areas for this method. The hybrid method works by taking a few baseline images. The treatment image is then fit to a linear combination of these plus a low spatial frequency polynomial phase shift. The polynomial phase fit reduces the errors seen in FIG. 34. Further, it reduces the sampling requirements of the multibaseline method (not as many multibaseline images need to be acquired). The hybrid method provides more robust results than referenceless or multibaseline processing alone, as shown in FIG. 34. With this method a temperature uncertainty below 2° C. in the septum was achieved using a interleaved spiral acquisition with 5 frames per second. Using a gated acquisition will allow for higher SNR and subsequently lower uncertainty. The hybrid reconstruction method is compatible with array coils, although reconstruction times increase with higher number of coils.

Once accurate temperature maps of the ultrasound heating are obtained, it is important that the temperature maps are registered to the correct tissue region in order to determine tissue coagulation and necrosis based on the temperature thresholds (~50-54° C.) and thermal dose ($t_{43}$>240) reached. Because the tissue moves and deforms during each cardiac cycle, the individual temperature images have to be registered to the correct anatomy. In one implementation, an algorithm proposed by de Senneville, et al. may be utilized for estimating the tissue displacement in the images. The proposed approach uses image-processing techniques to estimate real-time organ displacement from anatomical images. Image registration allows estimation of the organ displacement with subpixel accuracy because the registration process is computed with a large number of pixels. The objective is to register the coordinates of each part of the tissue in the temperature image with the corresponding tissue in a reference image. 3D vector field maps are preferred for this purpose, but they are difficult to acquire in real-time cardiac imaging. To overcome this problem, de Senneville, et al. have shown that estimating motion on 2D images generated by organs moving in 3D is possible. They quote a computation time of 200 ms for the registration of a 128×128 pixel image, which will be fast enough to allow for a real-time display of thermal dose and maximum temperature in our cardiac ablation application.

EXAMPLES

A series of empirical design trials were undertaken and a number of prototype devices tested. Initial efforts have developed prototype designs of catheters incorporating small ultrasound transducers capable of delivering high-intensity acoustic energy for localized thermal ablation. These preliminary efforts produced prototypes that have incorporated tubular, curvilinear, and flat small high-Q PZT transducers with associated power transmission lines and stabilizing mounting materials within a catheter delivery system. Multiple revisions and design of catheter extrusions and transducer assemblies during this process led to final devices which include lumens for RF power, contrast and fluid injection, acoustic coupling balloon, MR tracking coils, RF sensing lead, and an initial level of steering or deflection components. The development and pertinent test results of this progression are discussed and illustrated below.

Figure 1B:
Figure 1C:
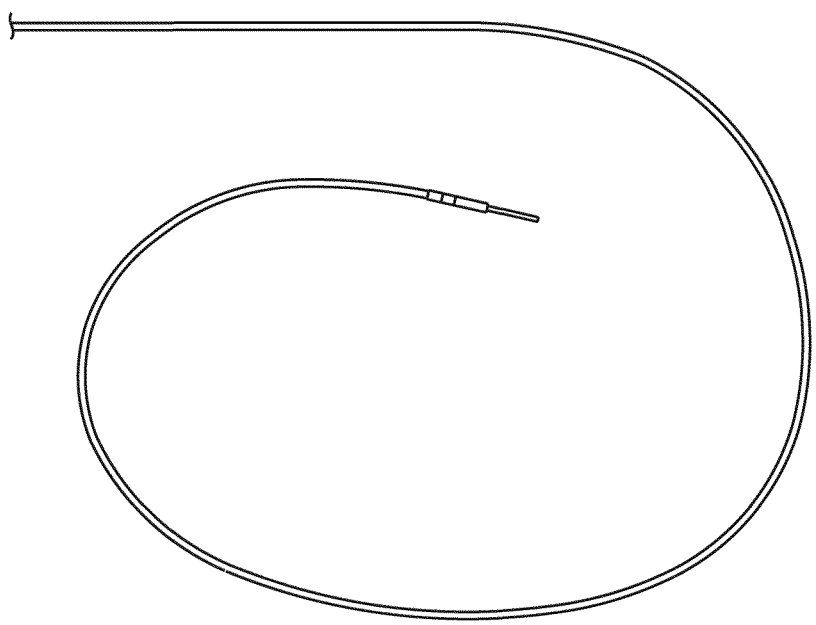

A prototype ablation applicators of ~2 mm diameter were designed and implemented using sectored tubular transducers (nickel plated) for preliminary evaluation. An example ablation device and schematics are shown in FIG. 1 (more details can be found in monthly progress reports). FIG. 1B illustrates an MRI-guidance catheter as an example of the general catheter size and flexibility desired for the ultrasound ablation catheter. FIG. 1C illustrates our first ultrasound ablation catheter prototype catheter with directional ablation transducer incorporated. Bench experiments with this device showed very good efficiency and acoustic performance. Thus, achieving the required acoustic intensity with small devices was demonstrated. This device, however, was not MRI-compatible, nor did it incorporate tracking coils for guidance, or other desired capabilities. Yet, this was the first implementation and achieved an initial ablation control performance goal for penetration and direction. The device of FIG. 1A includes a one or more supply lumens, a return for the cooling fluid, and a transducer. The placement of coils is shown at each end of the transducers, which may be held in place via bonding adhesives. In one implementation, a thermal sensor, such as a thermocouple, may be placed in the catheter, such as adjacent the transducer. In one implementation, the thermal sensor is placed just proximal the transducer to provide an indication of the temperature at the tissue. The thermal sensor may be part of a safety mechanism, such as to automatically shut down the transducer if temperatures exceed a certain threshold.

Figure 32:
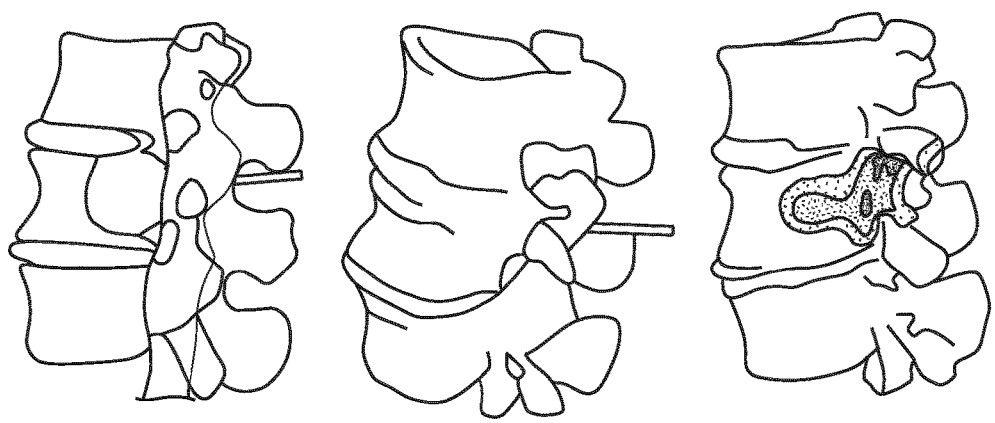
FIG. 32 depicts an MR directed transurethral multi-sectored applicator with fiducial coils for passive targeting of prostate ablation and a 2 mm MR directed vascular catheter with active RF tracking coils as developed in Phase I.

FIGS. 2 and 3 illustrate implementations of a device. The designs of FIGS. 2 and 3 are the candidates for fabrication of the devices for use in MR environment. In one implementation, the overall MR catheter drawing has an overall diameter of 2.7 mm, which is equivalent to 8 French. The final catheter extrusion met this goal, being 2.3 mm outer diameter. This incorporates an ablation transducer that is 1.7-2.0 mm cross section and 5 mm in longitudinal dimension. FIG. 32 illustrates an alternative implementation. FIG. 32 is an MR directed transurethral multi-sectored applicator with fiducial coils for passive targeting of prostate ablation and a 2 mm MR directed vascular catheter with active RF tracking coils.

Figure 4A:
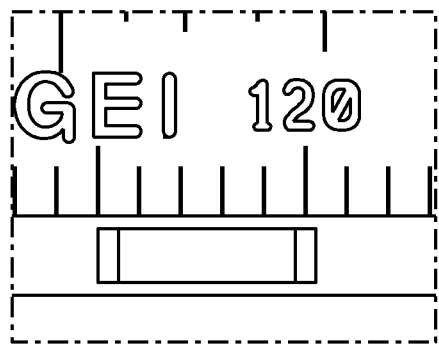
FIGS. 4A-4B is an Acoustic window (4A) and ablation transducer mounting (4B) on and within ablation catheter.
Figure 4B:
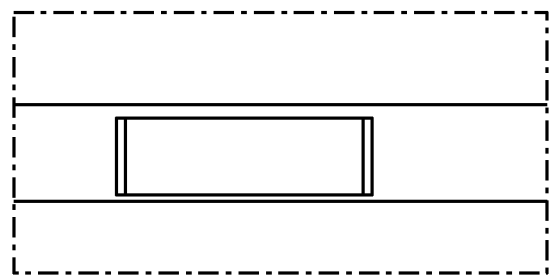

In one implementation, the ultrasound ablator is mounted on tubing such as polyetheretherketone (PEEK) Tubing. Following analysis and experimental iterations of methods for mounting of the piezoelectric transducer inside but near the inner lumen wall of the ablation catheter, it has been determined that using PEEK as a backing material produced the greatest efficiency and provided most protection for the fragile crystal material. An acoustic "window" was created which provided excellent transmission of acoustic energy with little attenuation. (FIG. 4). PEEK has low acoustic attenuation and is a strong and stable catheter material. It is also used, in one implementation, for backing of the acoustic ablator.

In one implementation having coil wires and guide wires, the lumen diameter sizes needed were 0.006" to 0.014" for coil wires, and 0.038" lumen (0.035" guide wire) for the guide wire. One lumen is needed for each of the two coil wires and two lumen for the guide wire for the NIH catheter. Another lumen is needed for the ablator wiring. Total wire lumens was thus five. Total Catheter OD was less than the size of an 8 French (0.10672.7 mm) catheter, which would allow a simpler route to the heart. A size as large as 12 French (0.158/4.0 mm) was determined to be a maximum. In one implementation, the durometer of the catheter is ~Shore 55A for most of the length with a preferred durometer for the distal end incorporating the transducer/coil area being ~Shore 40A. Integrate composite catheter of variable stiffness, with softer at tip—transition from current 55D to 40D at distal 5 cm. Other ranges of stiffness are achieved in different implementations, with the largest range being from 70D to 35D distally. Catheter bonding with same extrusion cross-section but with different materials can be implemented using several different bonding agents, for example, but not limited to heat-cured bonding and UV-cured bonding. Lumens aligned with Teflon mandrels and catheter heat fused. Technique will allow easier tip deflection. Deflection wires (nitinol) aligned to generate deflection to −90 degrees and ability to traverse 2 cm radius of curvature with transducer insonating direction preferentially oriented to the outside curvature.

For one implementation, it was determined that the optimum treatment depth would be 2.0 mm to 15.0 mm, and the transducer frequency would be close to 7 MHz to achieve that penetration range with good absorption efficiency.

In one implementation, the device has the ability to rotate and track the catheter easily to point the transducer at the area of the area (e.g., the heart) to be treated is required. Additionally, it is important that the ultrasound energy is effectively coupled to the target tissue (e.g., the heart wall). To ensure the applicator position could be tracked reliably, one tracking coil is placed distal of the transducer as well as one tracking coil proximal of the transducer. In one implementation, a MRI marker, such as one made from iron oxide, is used to help track the rotation of the applicator. The applicator assembly could be a separate entity from the outer catheter assembly with the goal of reducing the torque needed to rotate the transducer to the proper treatment orientation, and to allow the applicator to be pushed out a fixed distance for treatment. This also gives more protection to the transducer during its route thru the body to the treatment area.

In one implementation, AMS did preliminary work on the possibility of using the transducer measured reflected power to confirm applicator's contact with the heart wall. This work was performed in ex-vivo muscle tissue and the reflected power was clearly less with good acoustic coupling to tissue than when gaps existed in the coupling. AMS generated drawings of the applicator/catheter assembly design to help visualize the construction.

Initial devices incorporating the directional planar/curvilinear transducer design were fabricated using available single lumen catheter material of appropriate diameter obtained from Dunn Industries. Small Polyimid tubing was used for power and cooling lines and placed within the 2 mm OD outer catheter material. The active ablation region was near the distal end of the ablation catheter. The pattern of acoustic field was highly directive in the direction defined by the transducer location. The active transducer ablation region was 5 mm in length by 2 mm width. Depth of penetration depended upon applied power and time of insonation. Achieving a range from 2 mm to 15 mm was readily attainable. PEBAX® catheters were found to be too soft for minimizing rotational hysteresis. The isoplast nonelastic polyurethane is much better suited for use this implementation, both from a bonding and torque standpoint. A catheter was fabricated from this material and was tested acoustically, thermally, and mechanically, with good results.

Figure 7:
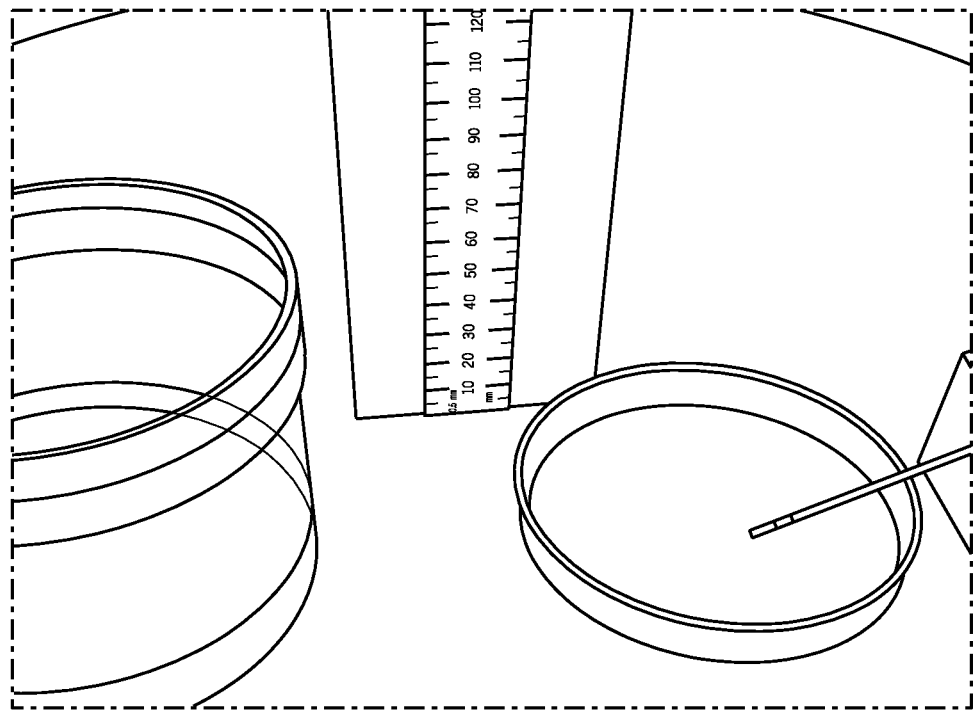
FIG. 7 is an Acoustic pressure wave generated water "fountain" with 8 watts input drive power.

Applicators and ablation configurations were fabricated and bench performance tested. Depictions of the 90 cm applicators are shown in FIG. 6 and water pressure testing at 8 watts electrical drive power are included in FIG. 7.

Figure 5:
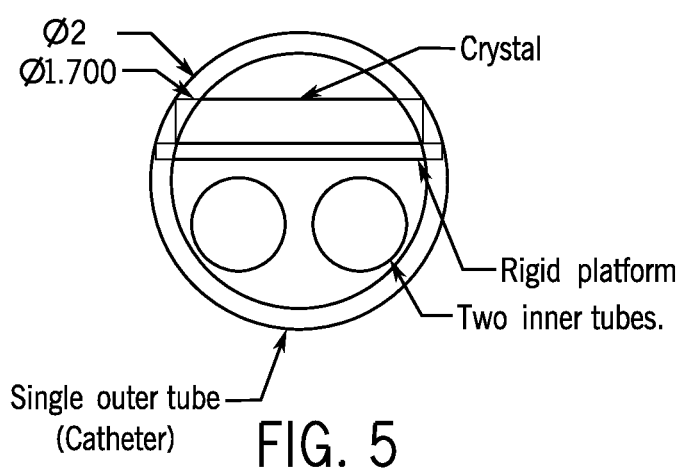
FIG. 5 is a cross-sectional view of one implementation of a catheter having a transducer crystal on a rigid support.
Figure 6A:
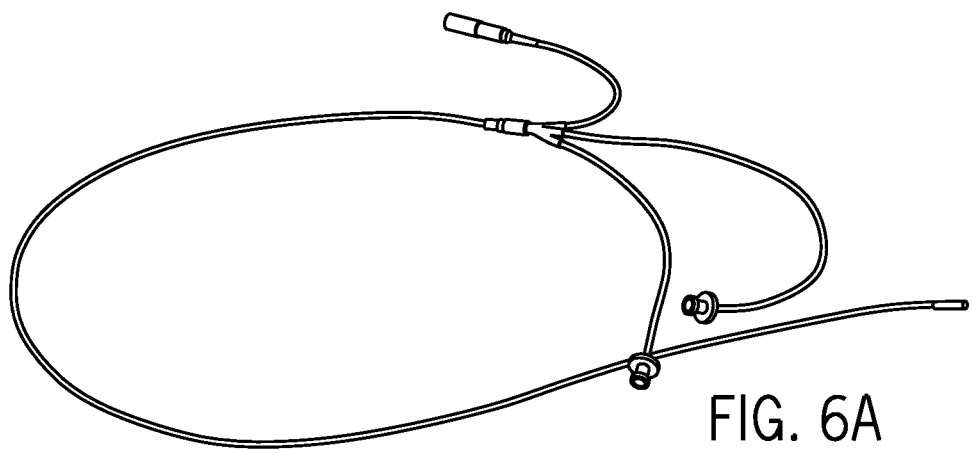
FIGS. 6A-6D illustrate different views of an ultrasound ablation catheter. 6A—view of overall catheter; 6B—second overall view of catheter; 6C—closer view of catheter showing coupling fluid inlet and outlet tubes/ports and power connector; 6D—closeup of US ablator distal portion of catheter with coupling balloon.
Figure 6B:
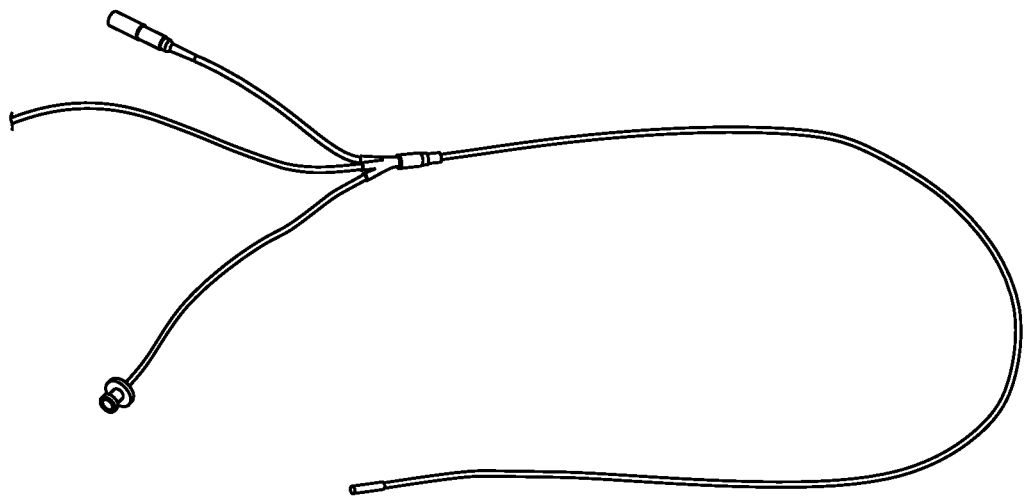
Figure 6C:
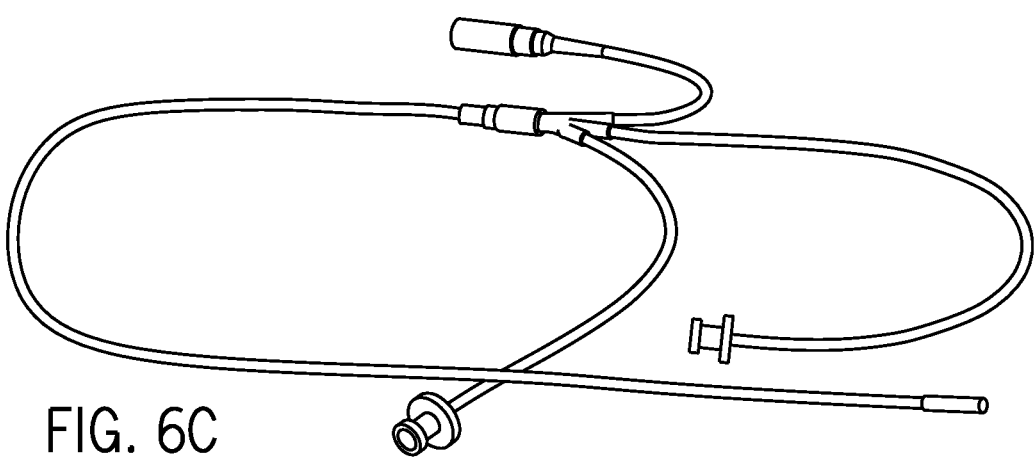
Figure 6D:

One implementation of catheter is a 90 cm long ablation catheter made from a 2 mm OD single lumen extrusion and polyimid inner tubes were used to supply power and return cooling for the transducer at the distal end. A cross-sectional drawing of this test catheter design (as fabricated and tested) is shown in FIG. 5. A ridged mounting surface was used for mechanically mounting the transducer crystal for added structural stability during use. The test ablation catheter was fabricated using this new mounting method. The mounting material used is nonporous high alumina ceramic. The test ablation catheter was fabricated using this new mounting method. Different material types for bend radius (2 cm) during inner catheter insertion of outer catheter were tested. The available PEBAX® catheter failed the minimal rotational loss during rotation of the ablation catheter due to being too soft and of insufficient durometer. A different sample of isoplast non-elastic polyurethane performed very well in the rotational test, even when 90 cm in length, with minimal difference between rotational angle at proximal and distal end of the catheter.

Figure 8:
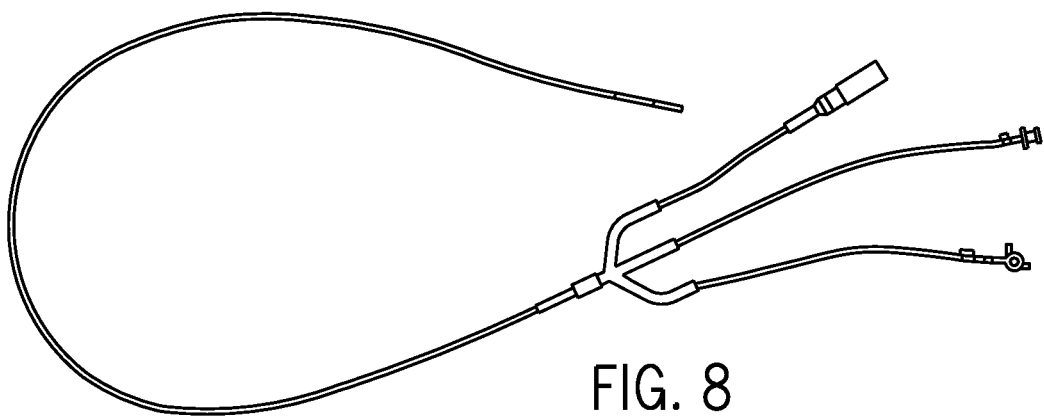
FIG. 8 is an overall view of second generation 90 cm length ablation catheter fabricated from extruded multi-lumen PBAX.

Additional 90 cm long ablation catheters were made from a 4 mm OD multi-lumen catheter extrusion with sufficient channels for all wires and water channels. A depiction of this catheter is shown in FIG. 8. This performed very well. The material is PEBAX having a durometer of 60. This higher durometer worked much better for rotation than the previous material, with excellent angle tracking results. This version tested the higher durometer material and a multi-lumen design, but exceeded the outer diameter specification. Yet, it did provide verification of the design approach.

Figure 9:
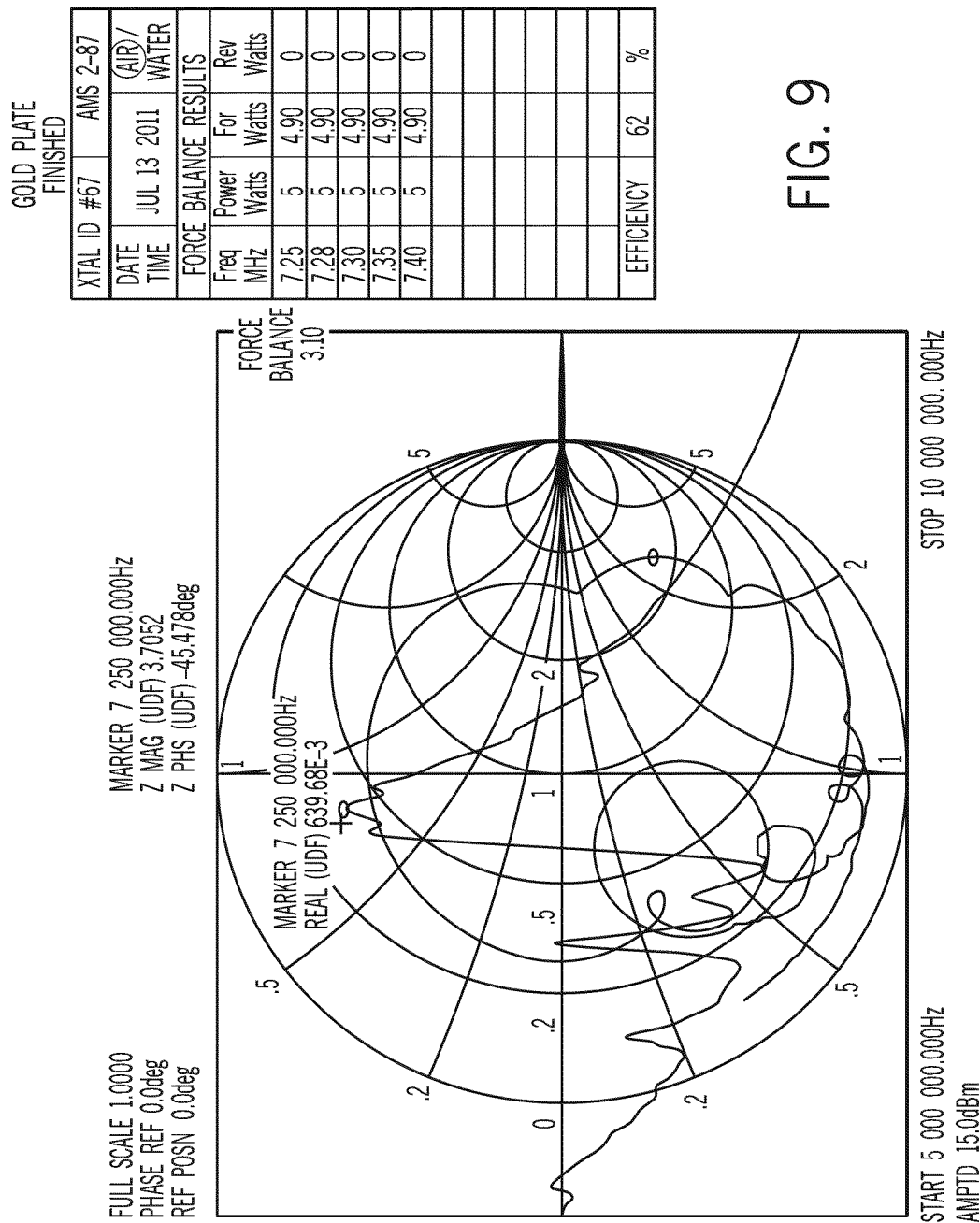
FIG. 9 is a Smith Chart plot of transducer impedance measurements for latest design. The central curve indicates good values for real impedance that matches the driving generator impedance. Additionally, the large circle indicates uniformity of performance of the device. The peak is at a frequency of 7.25 MHz with an efficiency of 62%.

A Smith Chart impedance plot for the transducer used in the catheter of FIG. 8 is shown in FIG. 9. Efficiency of the electrical to acoustic power of the ablation catheters was measured using a pressure force-balance measurement system. The conversion efficiency for the 90 cm length ablation catheters from electrical input to ultrasound output ranged from 50% to 65%, with current designs yielding >60%. An efficiency of 60% is considered to be excellent. Characterization of performance of US ablator devices is one key factor in achieving highly controlled results.

Tip-Steering

Figure 10:
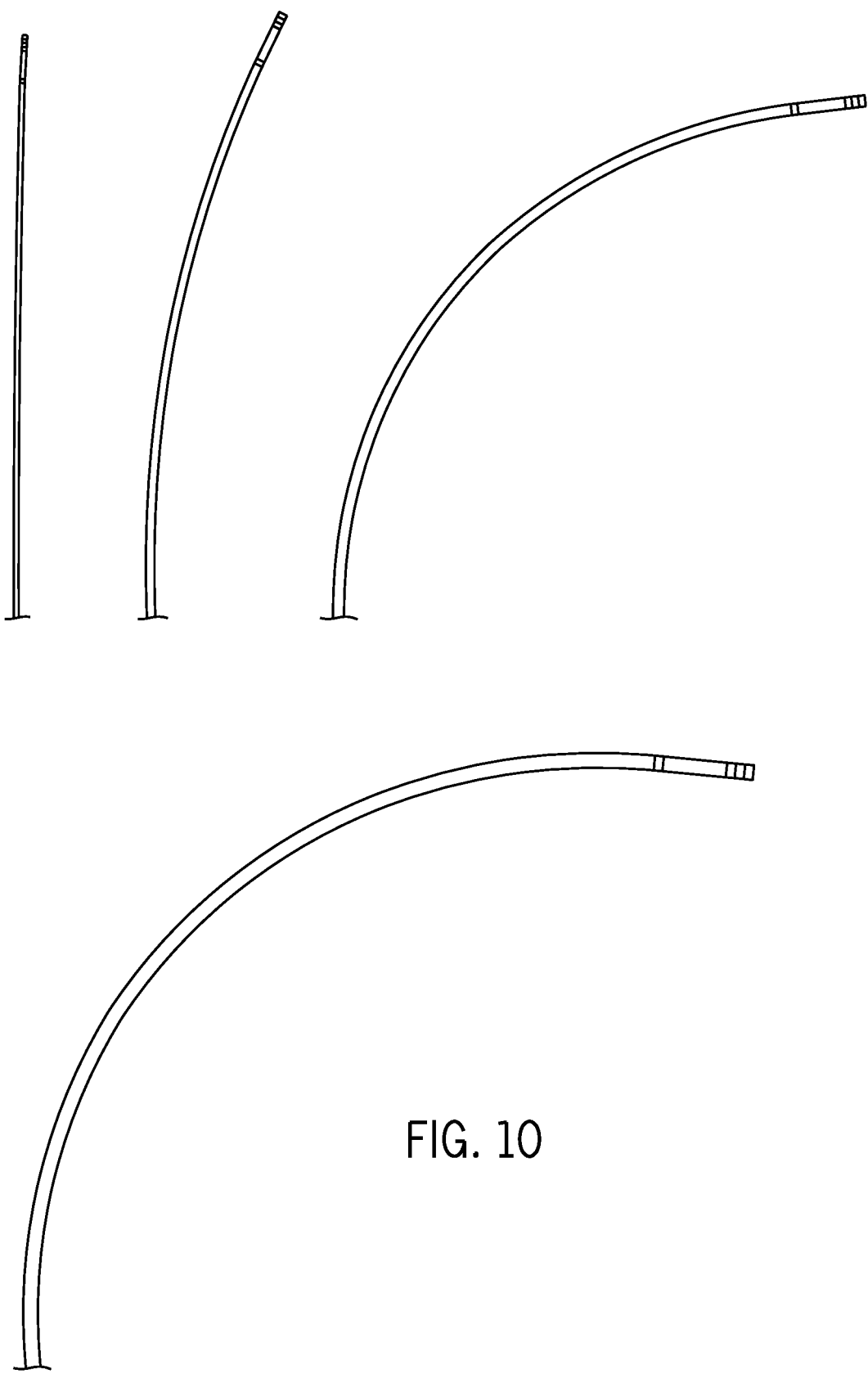
FIG. 10 depicts steering of distal end of ablation.

Certain implementations facilitate manipulation and steering of the catheter tip during insertion and placement through the use of the catheter and steering wire. Special lumens within the catheter have two guide wires, e.g. Nitinol, placed in opposing outer small lumens. The stiffness and length of the wires were determined to provide the best rotational stability/torque and tracking, and better steering than in earlier single lumen designs having inner channels of separate polyimide tubing inserted. The deflection capabilities and range are shown below in FIG. 10.

Catheter Extrusion, Fabrication Considerations and Testing

Figure 12:
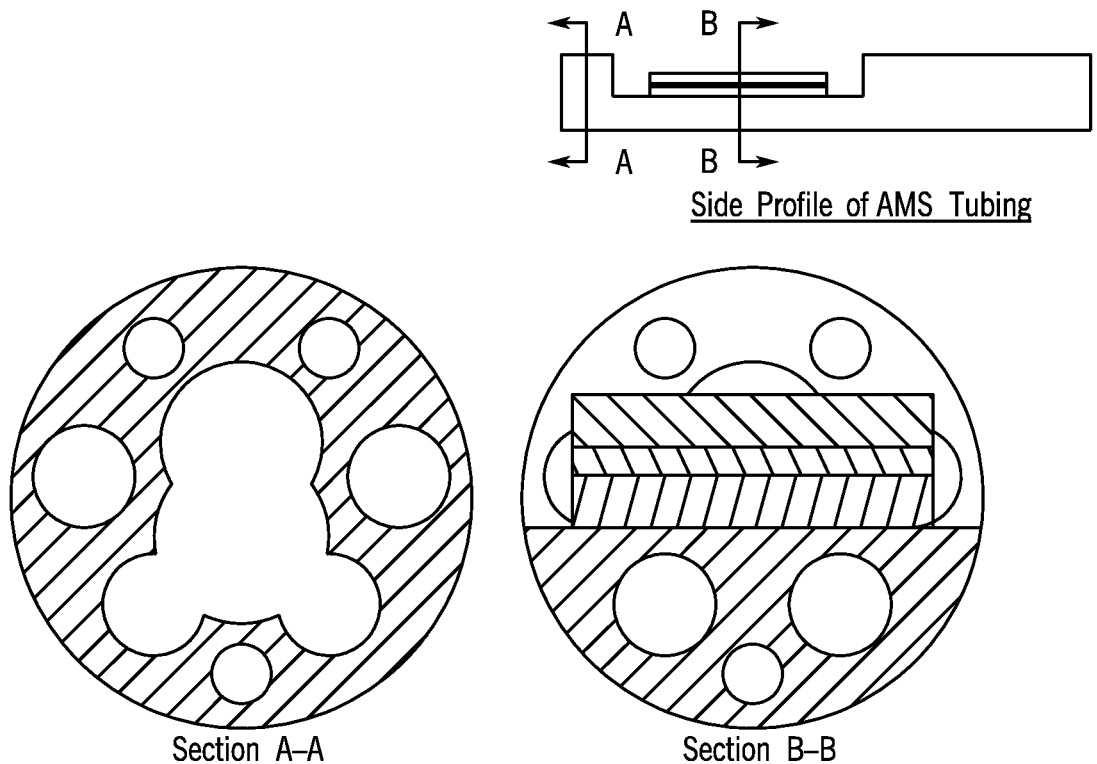
FIG. 12 is a side view of catheter showing mounting of ablation transducer and cross-sectional views of the mounting of the transducer and changes in lumen structure at distal end of the ablation catheter.
Figure 13:
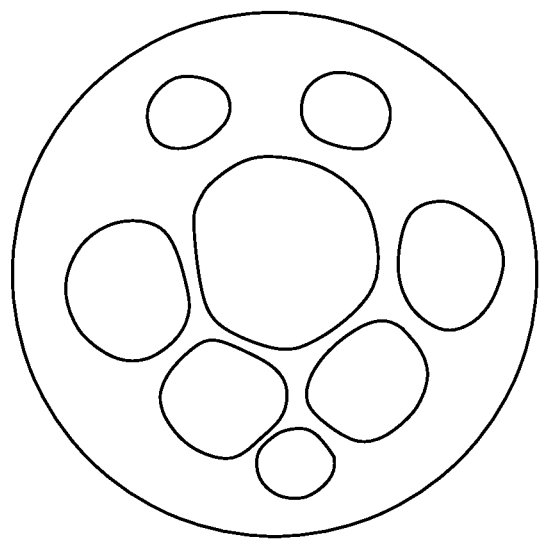
FIG. 13 is a cross-sectional view of final custom extruded ablation catheter design implemented.

One implementation of an ablation catheter was designed to 1) improve guidance and rotational control, and 2) meet or better the outer catheter diameter specification. Such a catheter is shown in cross section in FIG. 11. A total of 80 catheters, each 100 cm in length were received for testing. A side view of the ablation catheter showing the transducer mounting and two cross sectional views through longitudinal sections of the catheter at the mounting location of the therapy transducer are shown in FIG. 12.

The total diameter of the extruded catheter material was specified at a diameter of 2.2 mm. Following iterations and revisions, the final multi-lumen extruded catheter design was manufactured. All issues associated with mounting, bonding, power feed, fabrication, and performance were successfully resolved. Final ultrasound ablation devices were fabricated for testing using the new custom extrusion and tested at our facility in ex-vivo tissues. The outside diameter was 0.087" which was 0.002 greater than specified diameter, but within tolerance limits. The lumen sizes were also within the tolerance limits per FIG. 11.

In one implementation, coils were designed be integrated in an outer catheter sheath which would be around the ablation catheter.

In one implementation, the catheter includes tracking coils. For example, active RF tracking coils will be integrated within the cardiac ablation applicators as fiducial markers and position fixation to rapidly determine device position and orientation of monitoring planes during MRTI procedure or for purposes of treatment planning. In one particular implementation, small solenoidal coils (windings of 2 mil copper wire) are embedded on the catheter surface and connected to individual receiver channels via microcoaxial cable within multi-lumens within the catheter. The number of windings and orientation should be optimized for the particular catheter diameter and a tuning circuit with capacitive matching at the distal applicator will be adjusted for 50 ohm matching (63 MHz, 126 MHz for 1.5T and 3T systems)—this is following procedures applied for intravascular catheter tracking to guide/position catheters in 3D real-time for cardiac and neurological procedures. Two to three tracking coils will be used to quickly define device position and orientation within the heart. Similar developments for vascular tracking indicate positioning errors less than 1 mm are possible. Further, the detection of significant movement during therapy delivery can be treated as a safety feature, for example, possibly alarm for repositioning or reinitializing baseline temperature for the PRF MRTI. The pulse sequences can be modified and developed specifically for applications in cardiac ablation. Separate windings of 2 mil manganin wire can be used for generating passive fiducial markers as an aid to active tracking.

During the course of the testing, it was determined that the distal coil would be best integrated within the ablation catheter itself, in order to provide more accurate localization of the distal position of the powered ultrasound therapy transducer. The RF coil specification was a 20-turn coil of 0.09" diameter wound using 0.003 insulated magnet wire. The specified length was approximately 0.06". Two MR imaging coils were integrated on the ablation catheter, one proximal to the therapy transducer and one just distal, and used to demonstrate the feasibility of using MR tracking of the position of the ultrasound ablation catheter. Two coils were added to the catheter for tracking, with independent feed lines. Matching was determined and the custom catheter extrusion was used to fabricate candidate final ultrasound ablation catheters with MR tracking coils.

Flat transducer assemblies and curvilinear assemblies were fabricated to fit the new catheter. Preliminary power tests in water were performed to check transducer assembly integrity and efficiency at power levels from 2-6 watts (FIG. 14A-D). Additional tests included a rapid and reproducible test in color-changing cardiac tissue equivalent phantom. This is a useful method for performing quality assurance.

Operation of the Abalators

Figure 15:
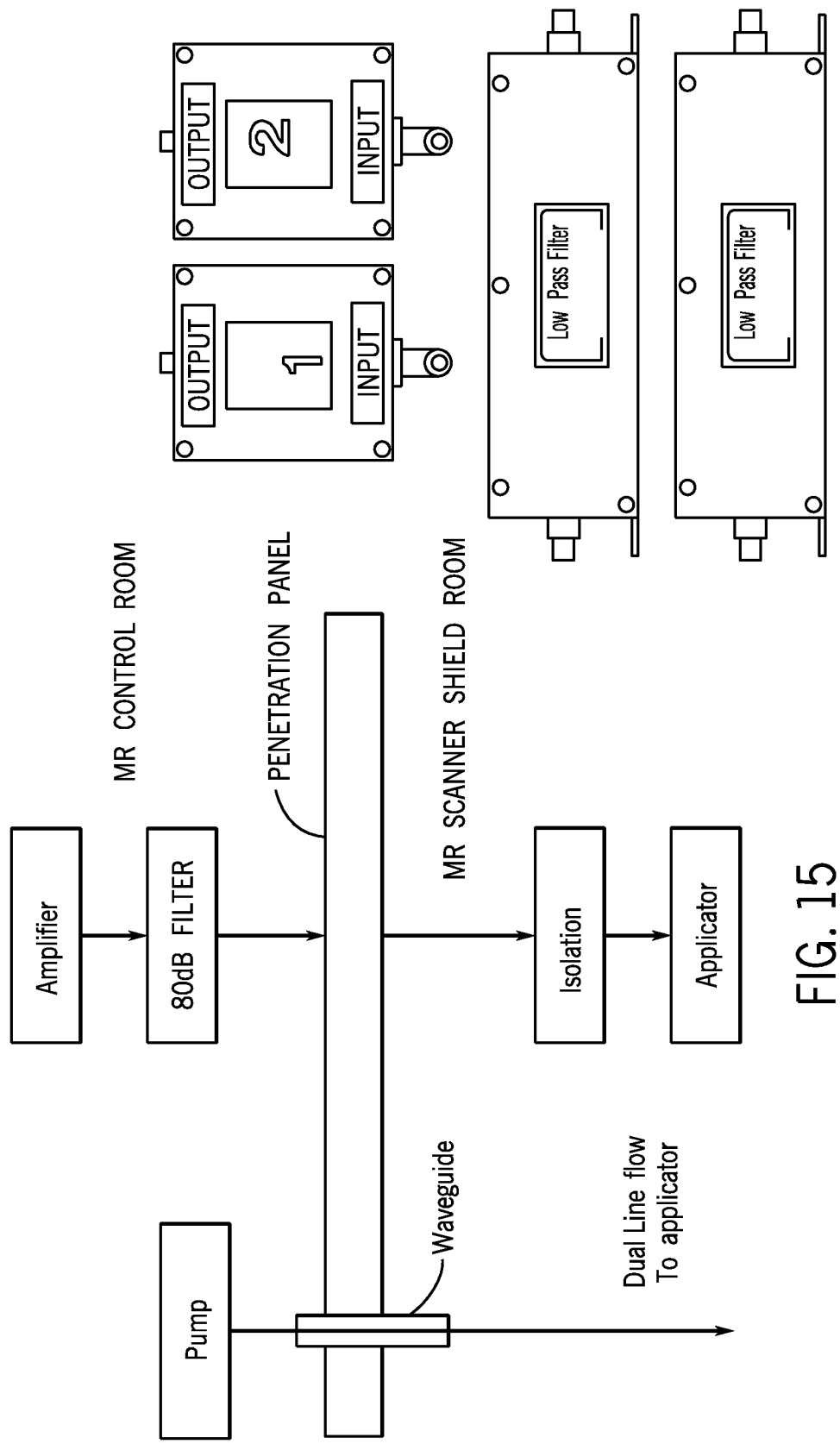
FIG. 15 is a general schema of Isolation transformers/DC blocks and RF filters and penetration panel setup developed for proper shielding of ultrasound devices during operation.

In order to operate the ultrasound catheter in an MRI environment, one implementation relates to a system of RF filters and compatible technology with the waveguides and BNC connectors on the penetration panel (FIG. 15). In one implementation, a system can include an RF system (amplifier and filters needed) and circulating fluid pumps all located in the MR control room (which may be separated by a penetration panel). The fluid cooling lines may be designed to pass within a 1 inch standard waveguide. Custom RF filters, for greater than 80 dB rejection of high-frequency RF noise that would interfere with 1.5 and 3T systems, with a pass-band up to 15 MHz have been designed for placement in-line with the RF output at the penetration panel. Isolation transformers with a 1:1 ratio have been fabricated to isolate the ultrasound device. Initial testing demonstrated excellent noise rejection and isolation during operation at high-power in an MRI environment. All connector cables and fittings within the MR shield room are MRI safe and nonferrous. The wiring through the penetration panel to the MRI suite and locations of filters and isolation transformers is shown in the left-hand panel of FIG. 15. The right-hand panel of FIG. 15 depicts both the isolation transformers and the RF low-pass filters.

Acoustic and Bioheat Thermal Modeling

A 3D bioacoustic-thermal model specific to ultrasound heating of cardiac muscle with a planar ultrasound transducer is implemented. Other implementations included convex and concave transducer configurations. This model is based on earlier work performed; however, the implementation for this application required implementation of a new model. The model was developed and used to investigate the impact of operating frequency, power levels, treatment duration and volumetric blood perfusion levels on the radial depth/volume of predicted ablation zones.

Figure 16:
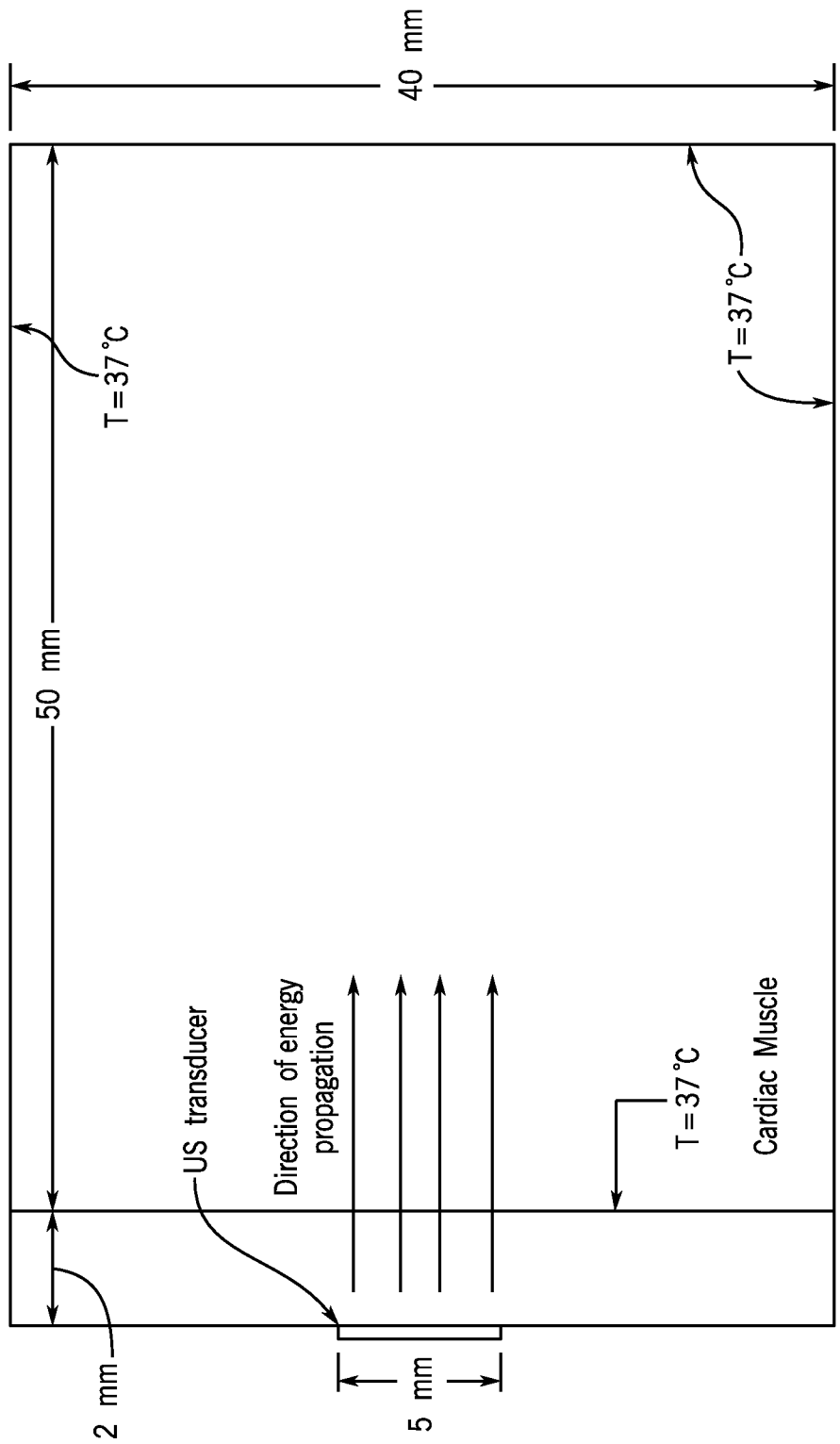
FIG. 16 notes the dimensions and thermal model parameters employed in the modeling analysis.

FIG. 16 illustrates the geometry used for model computations. The ultrasound transducer is assumed to be 2 mm away from the surface of cardiac muscle in order to simulate the effects of imperfect transducer-cardiac muscle contact, and cooling effects of blood flow. Constant temperature (T=37 CC) boundary conditions were used on the edges of cardiac muscle to simulate worst case heating conditions where blood flow maintains a constant basal temperature at the cardiac wall.

Heat-transfer in tissue during and after sonication with a planar transducer was calculated using the Pennes bioheat equation:

$$_p^a T_{at}^c = -V \cdot kVT + Q, rii_m c_{bi}(T - T_N)$$

The ultrasound heat sources, $Q_s$, was determined from the acoustic pressure field, given by the equation:

$$\frac{{}^a f 1 P}{\frac{{}^2 1}{P}}{C}$$

The rectangular radiator method was implemented (F=1000, grid size=0.1 mm) and used to determine the 3D acoustic pressured field due to a planar ultrasound transducer radiating in tissue. In order to determine the heat source, $Q_s$, pressure-squared profiles were down sampled before interpolation on to the finite element mesh. Table 1 lists tissue properties used for the simulations. The Pennes bioheat equation was solved using a nonlinear FEM solver implemented using COMSOL Multiphysics. Simulations were run for the following parameter combinations:
Applied power: 10 W cm$^{-2}$, 15 W cm$^{-2}$, and 20 W cm$^{-2}$
Heating duration: 30 s, 60 s, 180 s, 300 s and 600 s
Frequency of operation: 5 MHz, 8 MHz, and 12 MHz
Blood perfusion rates ($m_b$,): 2 kg M$^{-3}$ S$^{-1}$, 5 kg m$^{-3}$ s$^{-1}$ and 10 kg m$^{-3}$ s$^{-1}$

TABLE 1

Tissue physical properties used with the bioacoustics-thermal solver.

| Symbol | Parameter | Value |
|---|---|---|
| f | Operating frequency | 5-12 MHz |
| a | Ultrasound absorption coefficient | 10 Np/m/MHz |
| c | Speed of sound | 1540 m/s |
| p | Density | 1050 kg/m$^3$ |
| cp | Specific heat capacity | 3639 J/(kg K) |
| k | Thermal Conductivity | 0.56 W/(m K) |
| Mbl | Blood mass perfusion rate | 2-10 kg/m$^3$/s |
| Cbl | Specific heat capacity of blood | 3720 J/(kg K) |
| T$_b$, | Temperature of inflowing blood | 37°0 |

A total of 135 simulations were performed (3 power levels×5 heating durations×3 frequencies×3 perfusion levels=135). The heat-transfer solver was run for a further 120 s beyond the heating duration to account for accumulated thermal dose. For each simulation, we calculated volumes and radial depths (in cardiac tissue, does not include 2 mm spacing between applicator surface and cardiac tissue surface) of the ablation zone as predicted by the t43=240 min thermal dose threshold. This threshold has been demonstrated lethal to muscle and nerve tissue at these temperature and time exposures.

Figure 17B:
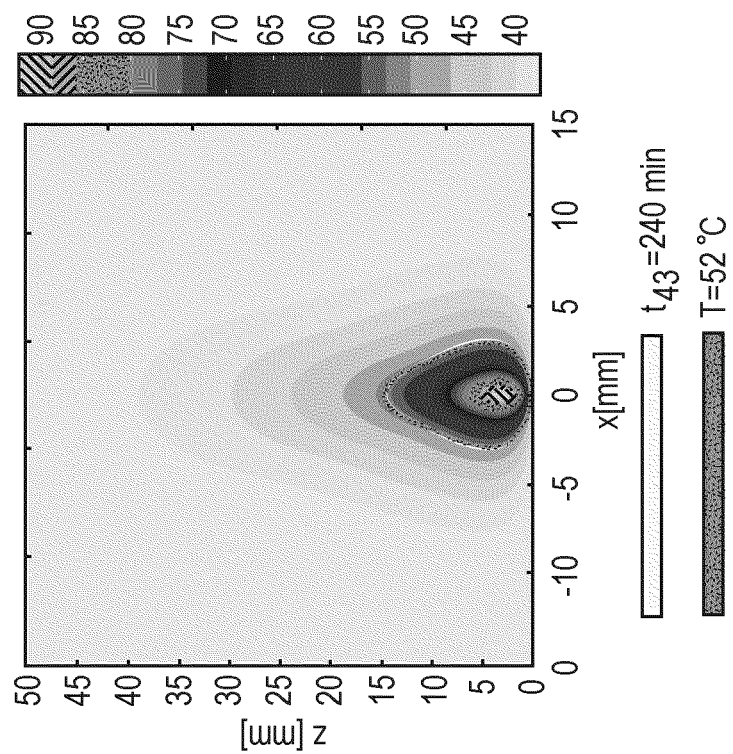
FIGS. 17A-17B—temperature profiles in yz (17A) and xz (17B) in cardiac muscle tissue after 60 s sonication at P=15 W/cm² and f=5 MHz.
Figure 17A:
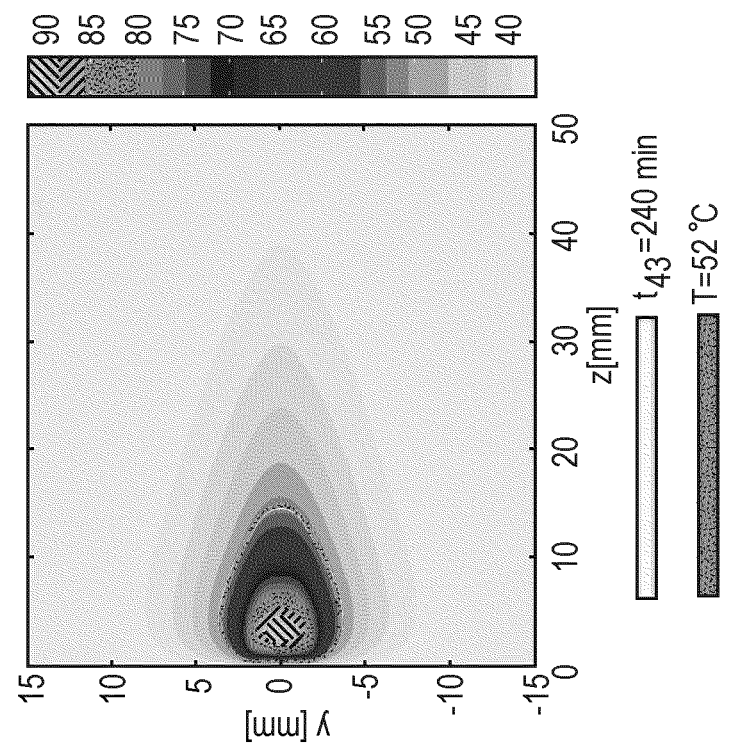
Figure 18A:
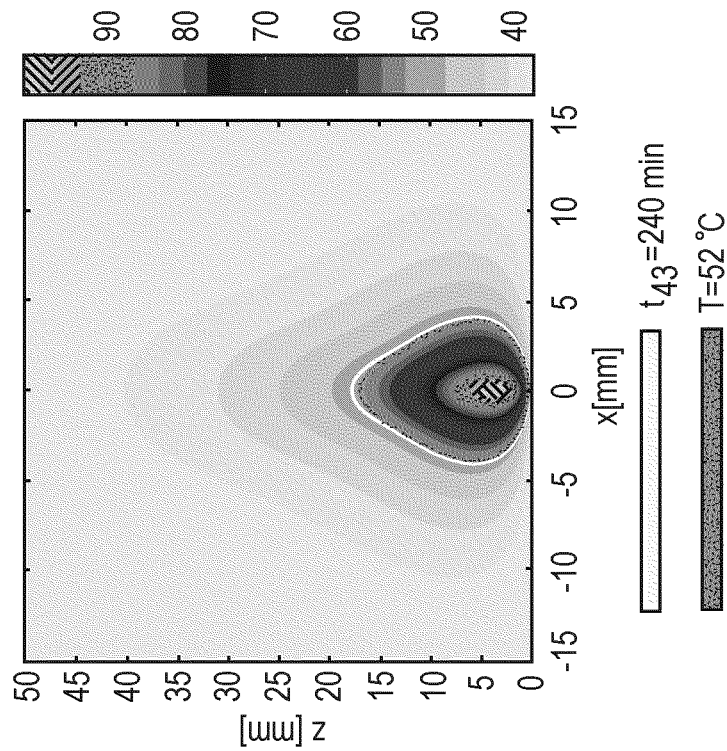
FIGS. 18A-18B—temperature profiles in yz (18A) and xz (18B) in cardiac muscle tissue after 180 s sonication at P=15 W/cm² and f=5 MHz.
Figure 18B:
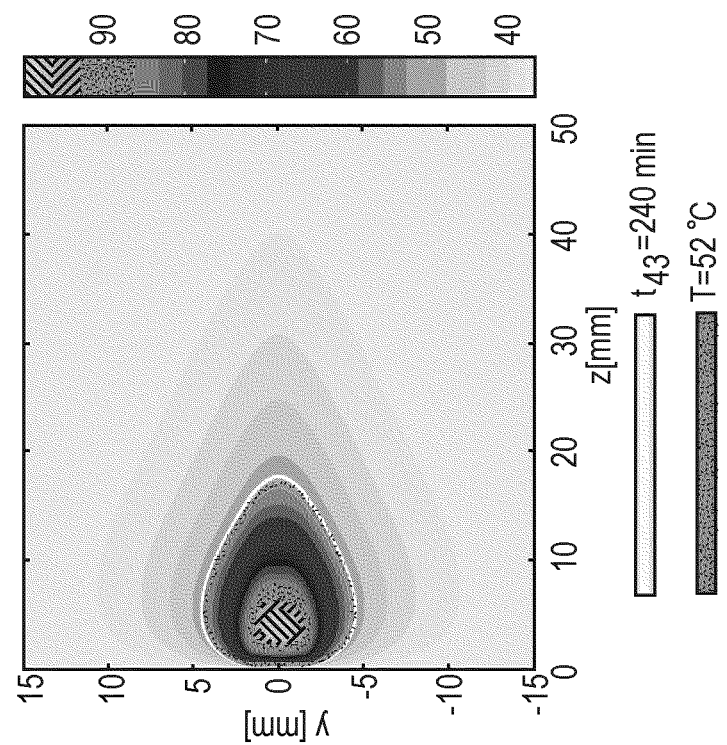

FIGS. 17 and 18 show sample temperature profiles (immediately before power off) after 60 s and 180 s ablations for applied intensities of 15 W/cm$^2$ and f=5 MHz. Also included are the $t_{43}$=240 min isodose contours corresponding to the predicted extents of the ablation zone. Thermal dose values were computed for 120 s beyond the ablation duration to account for any accrued thermal dose due to elevated temperatures after power supplied to the transducer was terminated.

Figure 19:
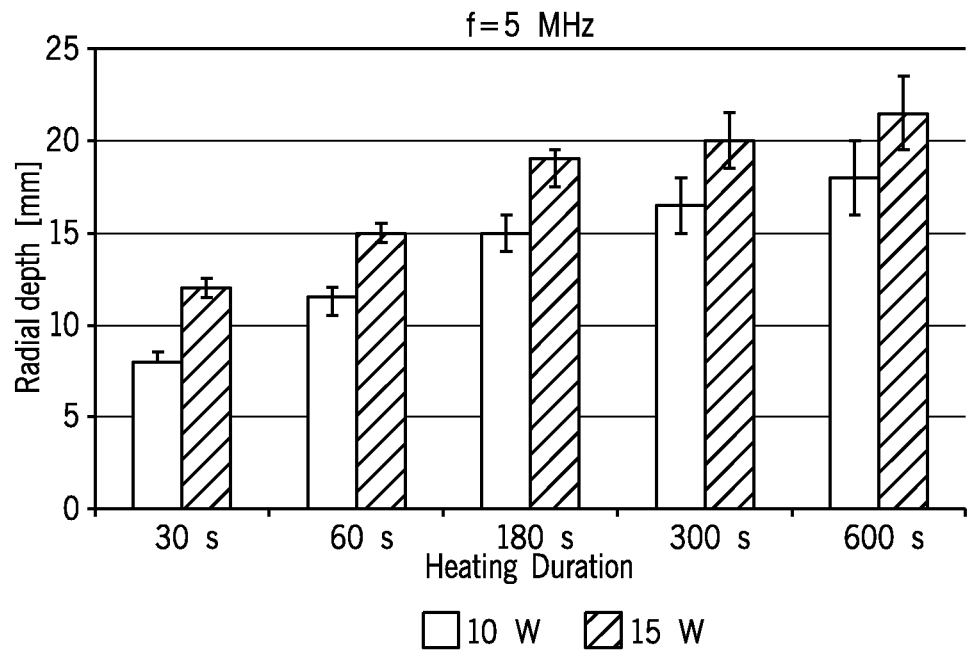
FIG. 19—max tissue temperatures remain <100° C. only at 5 MHz (of the frequencies considered). At 10 W/cm², f=5 MHz, $T_{max}$<100° C. for all heating durations. At 15 W/cm², f=5 MHz, Tmax>100° C. for heating durations 180 s, 300 s and 600 s. Error bars show range of lesion depth at different perfusion levels (2 kg/m³/s, 5 kg/m³/s, 12 kg/m³/s).
Figure 20:
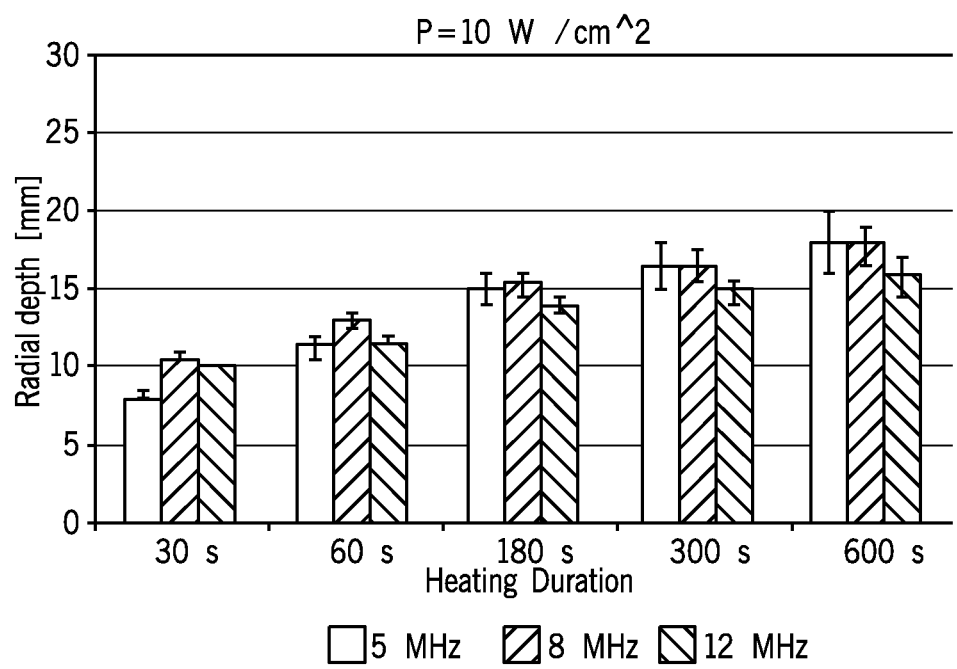
FIG. 20 has a radial depth of ablation zone as indicated by $t_{43}$=240 min dose threshold, after 30-600 s sonications, at f=5-12 MHz, P=10 W/cm².
Figure 21:
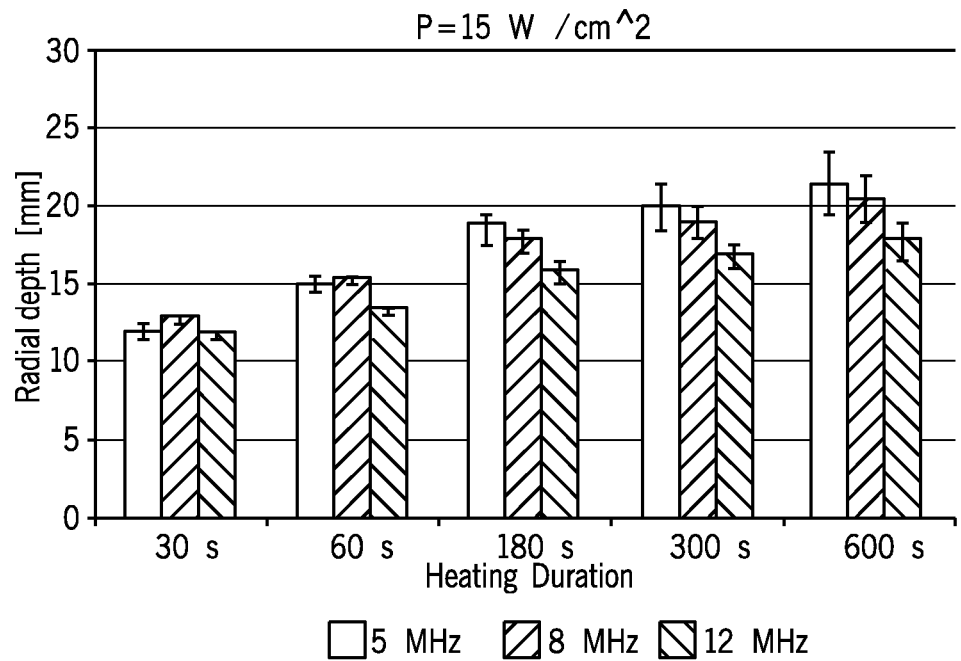
FIG. 21 has a radial depth of ablation zone as indicated by $t_{43}$=240 min dose threshold, after 30-600 s sonications, at f=5-12 MHz, P=15 W/cm²
Figure 22:
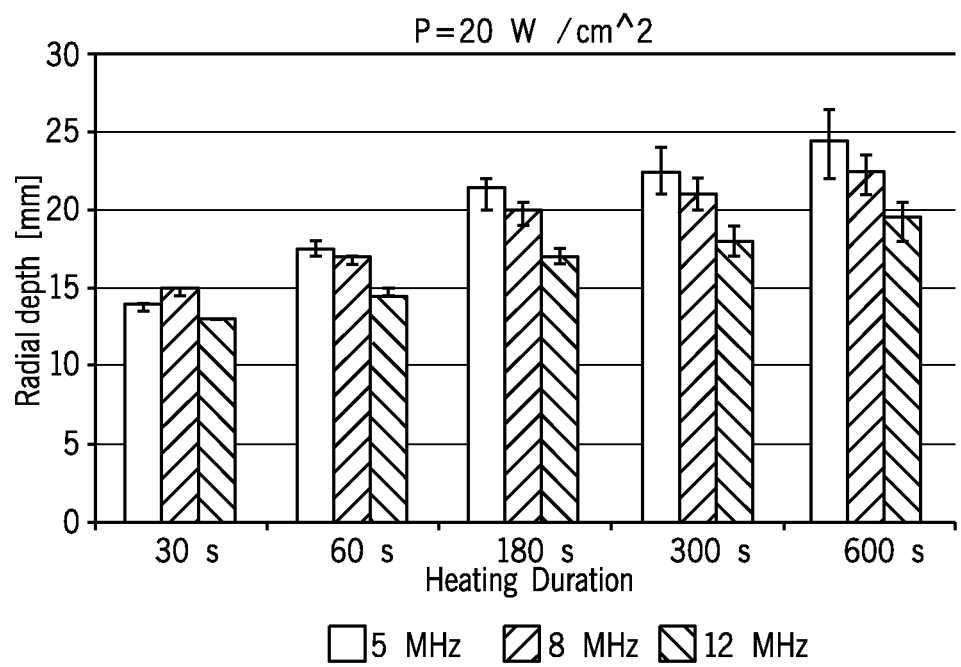
FIG. 22 has a radial depth of ablation zone as indicated by $t_{43}$=240 min dose threshold, after 30-600 s sonications, at f=5-12 MHz, P=20 W/cm²

The radial depth of the ablation zone (indicated by $t_{43}$=240 min thermal dose) varies with applied power levels, frequency, heating duration, and blood perfusion rates. FIG. 19 shows the calculated radial depth of the ablation zone for f=5 MHz at applied intensity levels of 10 W/cm$^2$ and 15 W/cm$^2$. At f=5 MHz and applied intensity of 10 W/cm$^2$, peak temperatures in tissue remained below 100° C. for the blood perfusion rates considered in this study. At f=5 MHz and applied intensity of 15 W/cm$^2$, peak tissue temperatures remained below 100 eC for heating durations under 180 s. For longer heating durations, peak tissue temperatures exceeded 100° C. At higher frequencies, peak tissue temperatures exceeded 100° C. for all heating durations and applied intensities. Note that these simulations did not incorporate a thermal heat sink associated with the latent heat of tissue water vaporization FIGS. 20-22 show the range of values for radial depth of the ablation zone, sorted by applied intensity levels. These simulations indicate that greater radial depths are obtained when using f=5 MHz or 8 MHz compared to f=12 MHz. In order to avoid tissue water vaporization and unpredictable heating that may occur as a result, f=5 MHz at applied intensity levels of 10-15 W/cm$^2$ appears to be most suitable for this application. At these applied intensity levels, ablation zone depths up to 15 mm radially can be achieved with 1-3 sonication.

In summary, the theoretical investigations demonstrated the anticipated performance of the ultrasonic ablator in vivo, indicating that thermal lesions 10-20 mm deep may be obtained within relatively short sonication times.

3-D Modeling

A 3D patient-specific modeling platform may be modified and applied specifically for certain applications, such as cardiac catheter targeted ablations within different areas of the heart. The optimal distribution of power levels supplied to devices is determined using a finite element method (FEM) model of bioheat transfer, implemented in COMSOL Multiphysics, coupled with a quasi-Newton optimization code within MATLAB. The model is described in detail in the prior art, but briefly the model uses numerically calculated or empirical beam data as input for power deposition patterns for transurethral ultrasound applicators, accounts for dynamic changes to acoustic attenuation and blood flow during heating, and allows for variable tissue parameters at each node.

Figure 33:
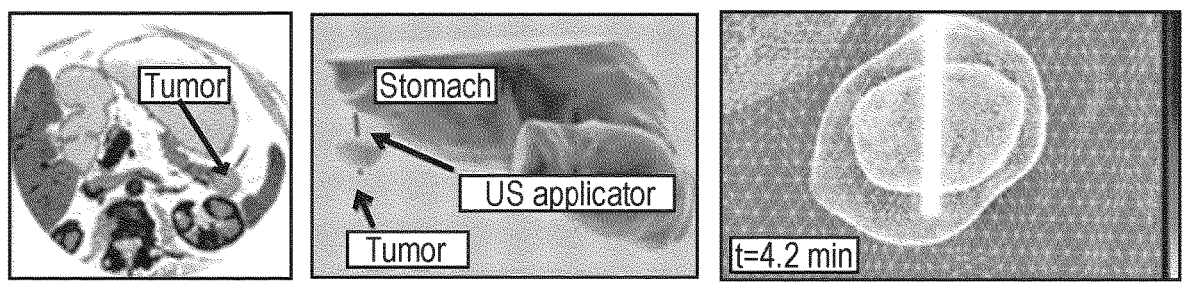
FIG. 33 has capabilities of therapy modeling platform to be extended herein include: heterogeneous and dynamic tissue properties, shown for catheter-based applicator tumor ablation for complex tissue models in (left) bone and the (center) abdomen; Reconstructed volumes, FEM mesh, 3D temperature maps are shown.

The accuracy of this model has been verified against in vivo and ex vivo lesions. Recent efforts have incorporated this model for more complex interventions specific to catheter based ultrasound in prostate, spine and pancreas (FIG. 33), including interactions with bone and air interfaces. Additional tissues or anatomic models may be used, but should account for more complex and convoluted applicator routes, critical structures (e.g., nerves, blood vessels, esophagus), and bone and air interfaces adjacent to or within proximity of the target volume. These complex geometries can be generated from serial CT or MR scans to build a set of 3D test cases. In one implementation, Mimics innovation suite (Materialise®) will be used to segment and construct these complex 3D structures with applicator placement, and generate the FEM mesh with tissue dependent acoustic and thermal properties. The absorption of ultrasound in bone structures is approximated by a fast hybrid absorption model Air interfaces are modeled as simple reflection. Large thermally significant blood vessels (>1-3 mm) and chambers of the heart are modeled using transient convective boundary and linear flow profiles, to define impact of vessel size, flow, and distance from applicator to resultant temperature profiles. Ultrasound applicator intensity outputs, characterized using needle hydrophone and acoustic displacement measurements, may incorporated for greater accuracy in estimating in situ energy deposition.

These improvements and applicator specific modeling will be coupled with optimization algorithms for determination of ideal positioning or coupling distance, applicator designs, applied power levels, and required durations. These models and the modeling platform may be used to develop and evaluate applicator design revisions and develop treatment delivery strategies. These models will be evaluated using temperature measurements obtained in phantoms and animal data as described below. This optimization based modeling and planning will also be used to generate detailed SAR, temperatures, thermal dose profiles, dimensions of lesions vs power and time, optimal power trajectory, and safety profiles for performance indices.

Ex Vivo Examples

Figure 23:
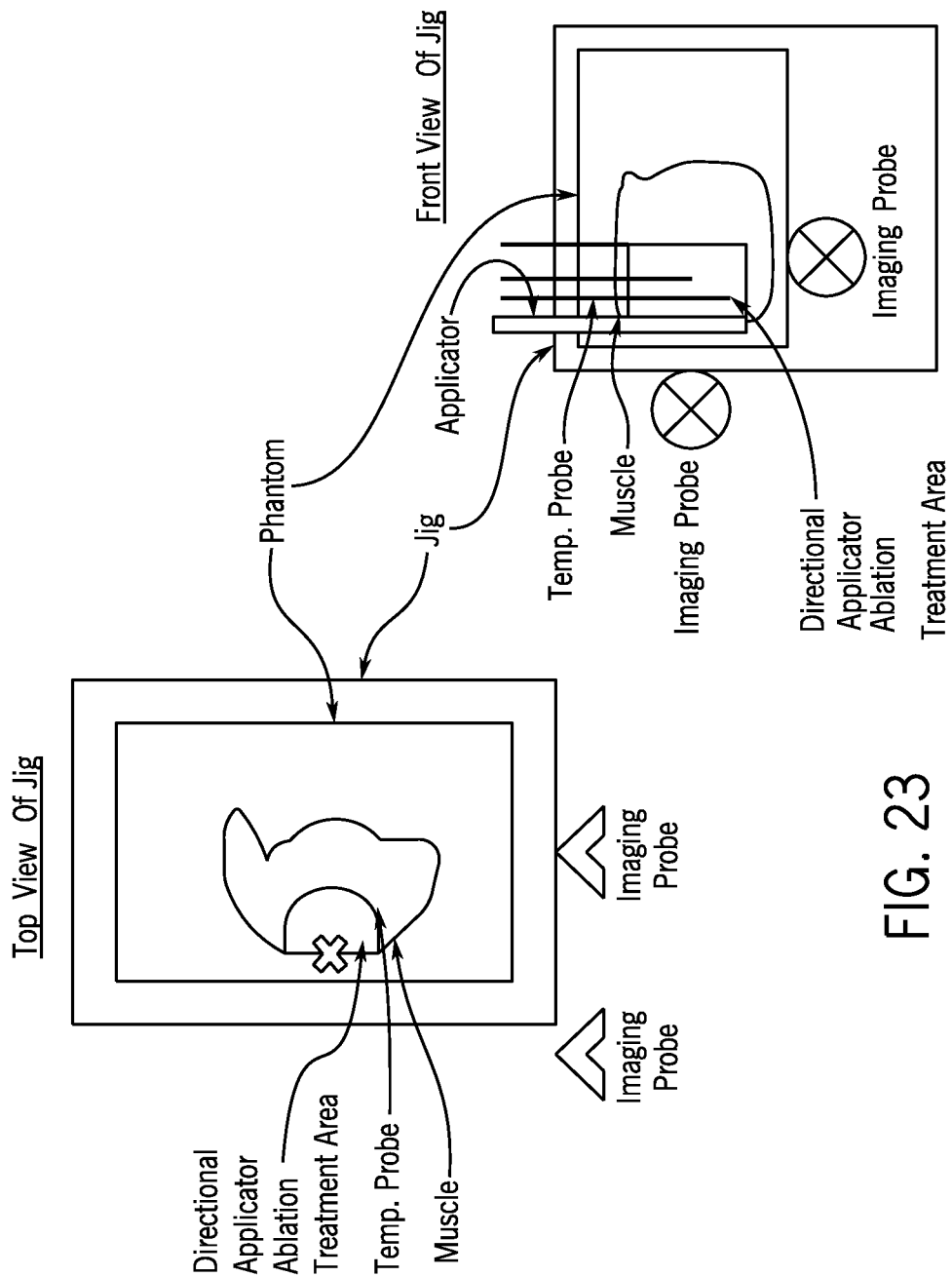
FIG. 23 is an experimental setup for ex vivo studies used for empirical design and performance studies. Note locations of the directional ablation applicator and the placement of temperature sensors and ultrasound imaging probes.
Figure 24A:
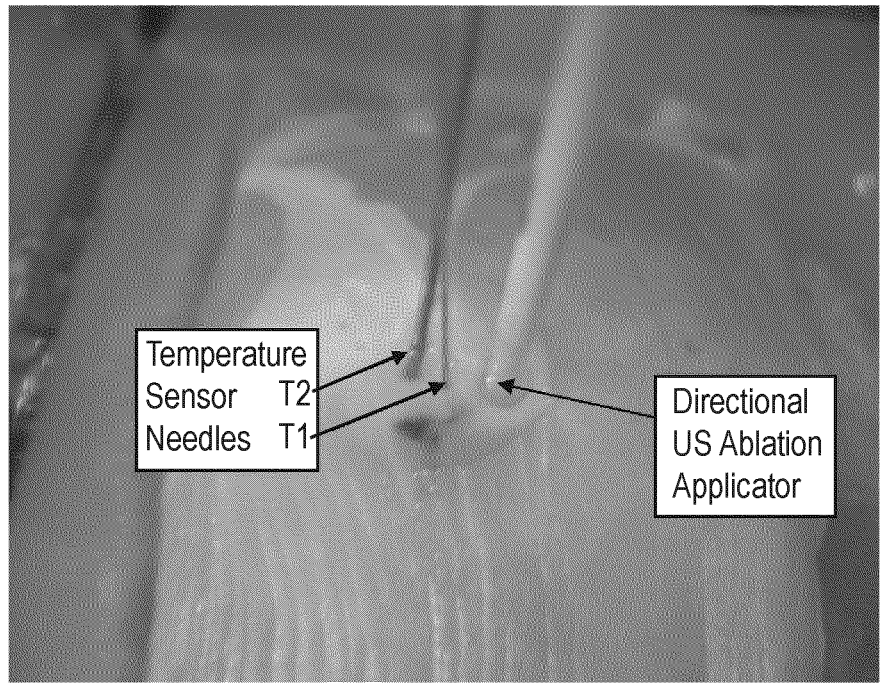
FIGS. 24A-24D illustrate testing of US catheter: (24A) US ablation catheter and sensor probes placement; (24B) ultrasound image of the tissue showing the longitudinal placement of the devices; (24C) temperatures achieved in different locations; (24D) thermal dose in target treatment zone (necrosis occurs at >250 achieved at 50 sec; 5000 achieved at 75 sec).
Figure 24B:
Figure 24C:
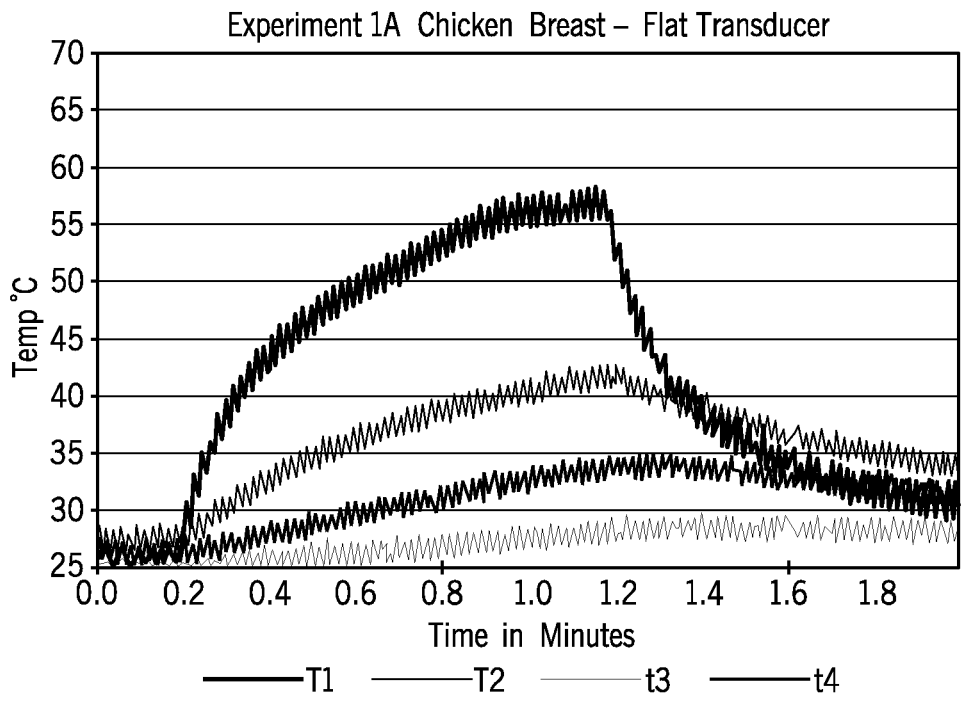
Figure 24D:
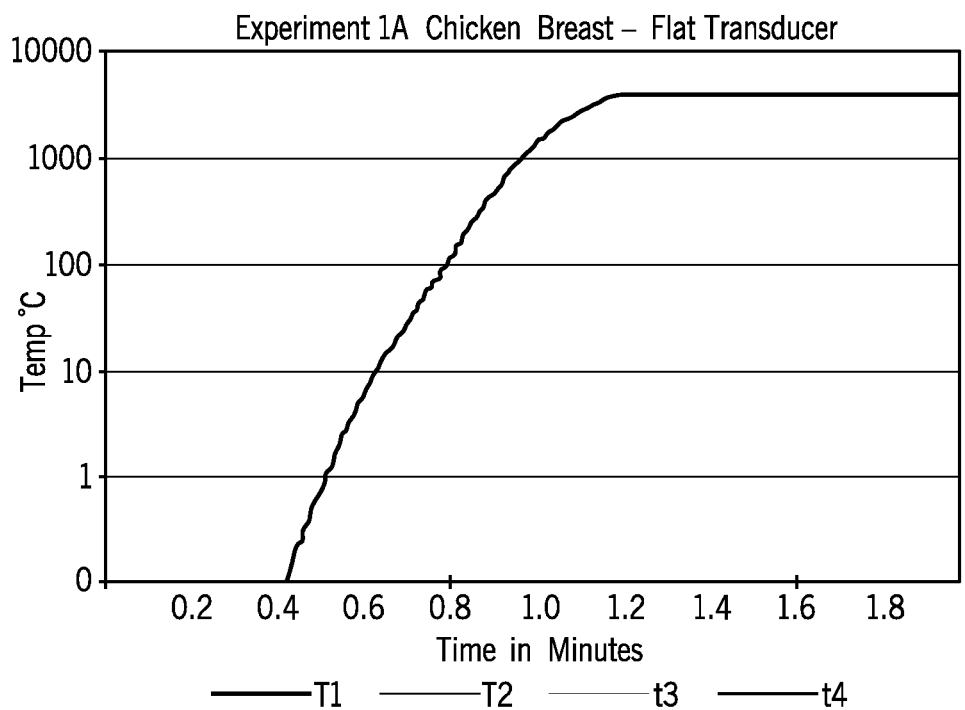

A series of experiments were performed in ex vivo chicken muscle, cardiac muscle and beef liver to evaluate the performance of the POC ultrasound ablation catheters. Temperature sensors were placed at positions that would represent the desired depth of thermal lesions in cardiac tissue. The position of the temperature probe and sensors was verified using ultrasound imaging. During the sonication sequence the temperature was monitored and real-time accrual of thermal dose was calculated. The experimental setup (FIG. 23) and some typical examples are shown below for test cases in chicken muscle (FIG. 23). These experiments provided feedback during the empirical design phase and also complete characterization of lesion capabilities of the final POC device prior to testing in the MRI.

An example result from one of the muscle tissue ex-vivo thermal ablation studies is shown in FIG. 24. A total of 12 experiments were performed ex-vivo, with 8 of them being using the final custom extruded ultrasound ablation catheter. FIG. 24A is a photo from above the specimen showing the placement of the directional US ablation catheter and two arrays of thermocouple sensors within two needles inserted at different distances of 5 mm and 9 mm from the catheter. FIG. 24B is an ultrasound image of the tissue showing the longitudinal placement of the treatment ablator and the two temperature sensor arrays. FIG. 24C shows the unfiltered temperature data versus treatment time for four temperature sensors. The third and fourth temperature curves were outside the directional ablation zone (within range but located to the side of the directional propagation of high intensity ultrasound). The sensor of the second temperature curve was placed at 9-10 mm distance from the catheter outer wall, at the distal edge of the treatment zone depth. The sensor of the first temperature was placed in the central portion of the targeted treatment zone and reached the highest recorded temperature. Thermal dose is shown in FIG. 24D corresponding to the first (T1) temperature.

Accuracy of Exemplary Catheter

Figure 25:
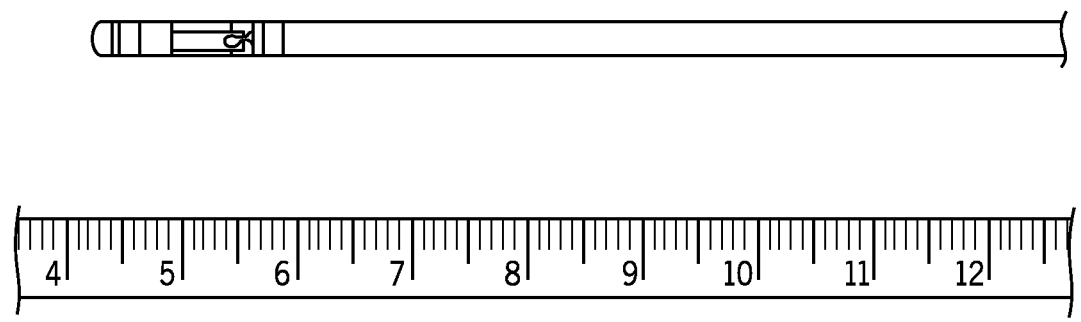
FIG. 25 is a final POC MR compatible US catheter.
Figure 26:
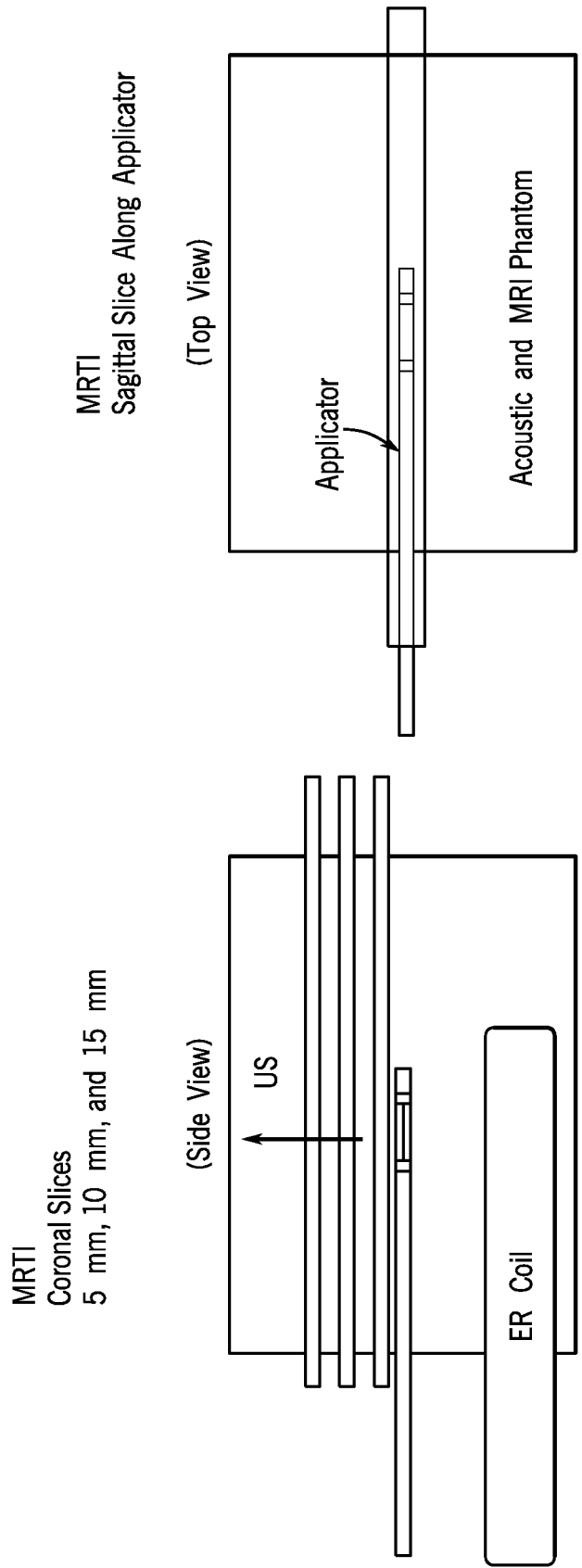
FIG. 26 is a schematic of experimental setup with applicator aligned with main B-field down bore of 3T MRI. (An ER coil and 4 inch surface coil was used in this particular setup, designed for prostate studies). Three coronal slices above the heating applicator (left) and one sagittal slice through the applicator lengthwise (right) were setup for monitoring. The phantom has acoustic, thermal, and imaging properties similar to cardiac tissue.

A series of experiments were performed to test the accuracy of the ultrasound catheter, and to measure the artifacts and thermal distributions of the POC cardiac applicator as measured in an MRI, and provide preliminary data supporting feasibility. The applicator under test (FIG. 25) was inserted into an MRI/Acoustic tissue equivalent phantom equilibrated at room temperature. MR temperature monitoring was performed in a sagittal slice through the length of the catheter, and in three coronal slices at 5 mm, 10 mm, and 15 mm distance from the active surface. The thermometry sequence is based upon the PRF technique. The test setup was adapted from a current setup to evaluate transurethral devices, so used an endorectal imaging coil placed beneath the device and embedded in the phantom, and a 4" surface coil on the top surface (FIG. 26). Magnitude images of the applicator within the phantom are shown in FIG. 27. Imaging sequence at 3T: 5 mm slice thickness, Gradient Echo TETTR=7/120, FA=10°, FOV 15 cm×15 cm, BW 10.4 kHz. MR temperature slices were updated in ~5 s intervals. Electrical power of 8 W at 6.3 MHz was delivered to the applicator for a period of 5 min (300 s). 80 dB bandpass filters and isolation transformers were integrated with the RF power delivery at the penetration panel. Immediately prior to power on, the baseline phase maps were recorded and the device water flow rate was set to ~30 ml/min of ambient water through the balloon. The tracking coils were not able to be tested due to 3T hardware issues, but problem is resolved for next time testing is done.

Figure 28:
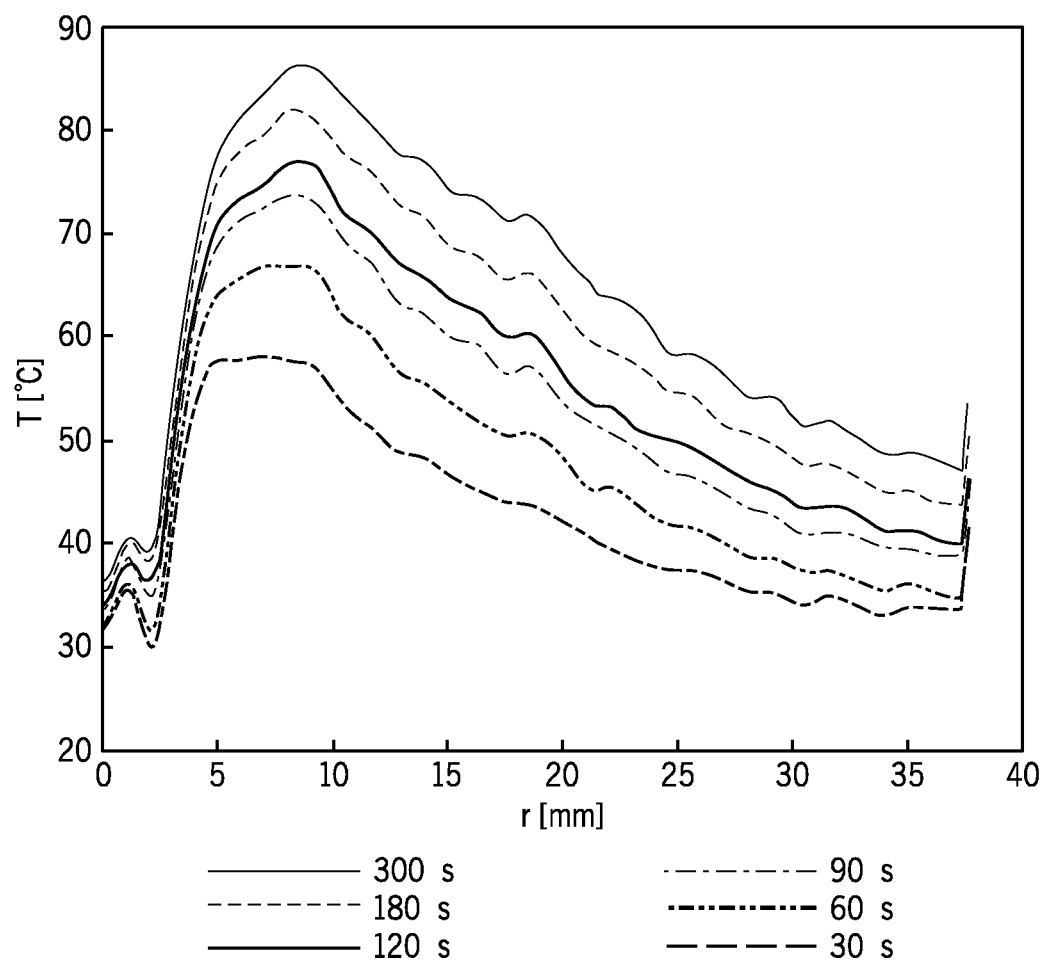
FIG. 28 has MR temperature measurements during a 5 min sonication at 8 W drive power, as measured in the sagittal slice through the applicator. Profiles at 30 s, 60 s, 90 s, 120 s, 180 s and 300 s are shown. The scale is 15 cm×15 cm. The catheter is oriented vertically and located at the center of the image. Insonation is directed to the right away from the catheter. As shown by MR thermal imaging, effective penetration into the cardiac tissue equivalent phantom is several mm at 30 s to nearly 3 cm at 300 s. Length of ablation along catheter just slightly longer than the active transducer crystal length, which is 5 mm.
Figure 29:
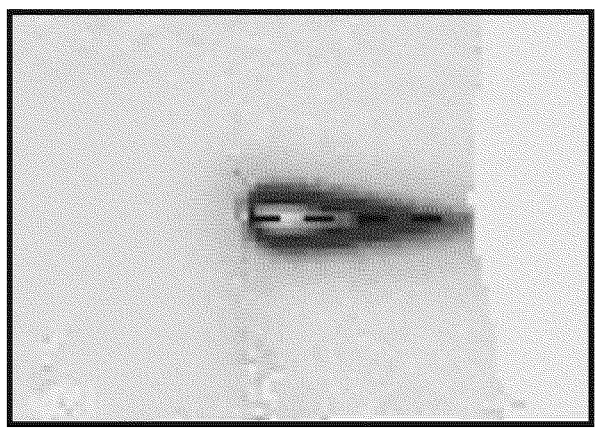
FIG. 29 has MR transient temperature profiles in distance from the applicator surface, as measured in the central heating plane. Central line (dashed black line) is demarcated for measurements. Note that effective thermal penetration is from 5 mm to >30 mm and can be varied and controlled as a function of time and/or power.
Figure 30:
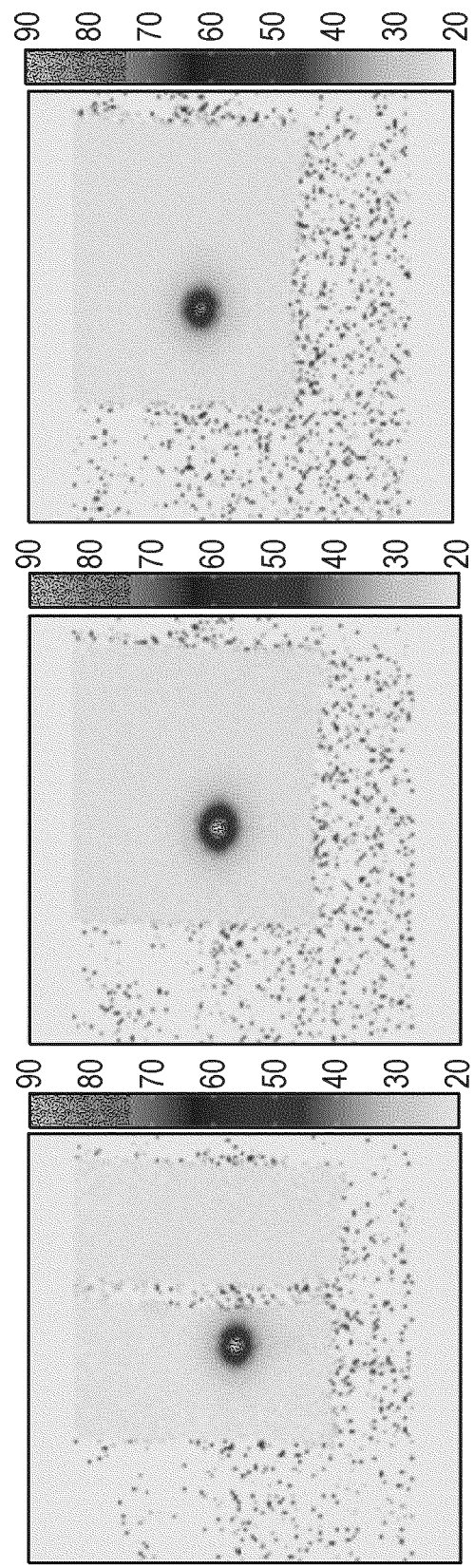
FIG. 30 has MR temperature distributions measured in coronal slices at 5 mm, 10 mm, and 15 mm (left to right) above applicator surface at 180s time point. A band of artifact in (a (leftmost image)) is a result of bands from the sagittal slices being simultaneously monitored. The scale is 15 cm×15 cm.
Figure 31:
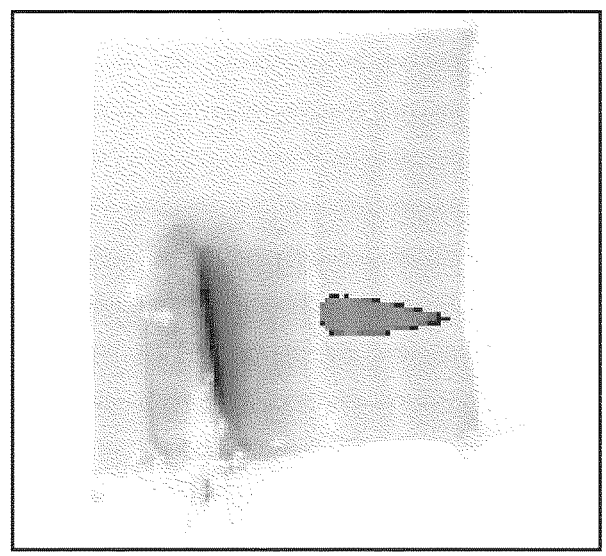
FIG. 31 has a thermal dose map at 300 s time point: t43 maps (first, outer) black=50 min, (second) dark gray=240 min, (third, center) gray=1000 min. t43>240 min is thermally destructive to cardiac nerves. The scale is 15 cm×15 cm.

The MR temperature maps at 30, 60, 90, 120, 180, and 300 seconds as measure within the sagittal plane (FIG. 26, right) are shown in FIG. 28, and demonstrate directional and precision heating of a target zone off the distal end of the device. The thermal penetration as a function of time as measured in a central line from the center of the applicator is shown in FIG. 29; clearly showing therapeutic or thermal necrosing temperatures that extend up to 30 mm from the applicator (at 300 s) and can be controlled with treatment duration and/or power. As shown in FIG. 30, the temperature distributions in coronal planes across the target area at 5 mm, 10 mm, and 15 mm distance from the device demonstrate well localized therapeutic distributions. The noise level during application of RF power was negligible. The artifacts in images are also small. The final thermal dose distribution is shown in FIG. 31, where 240 EM at 43° C. is nerve destructive.

The cardiac ablation catheter has negligible susceptibility artifact and RF noise artifact during operation, and is compatible with measurement and use in 3T. MR temperature monitoring has demonstrated localized and fast thermal ablation extending up to depths of 10-15 mm within short operating times.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A catheter device for treating tissue with ultrasound comprising:
    an inner catheter comprising:
        an ultrasonic transducer mounted on a rigid platform disposed within the inner catheter at a distal end of the catheter device defining a catheter device tip; and
        a first radiofrequency (RF) tracking coil integrated within the inner catheter; and
        a first plurality of lumens; and
    an outer catheter around the inner catheter, the outer catheter concentric with the inner catheter and comprising:
        at least two guide wires disposed within the outer catheter;
        a second RF tracking coil integrated within the outer catheter provided at a location proximal the ultrasonic transducer relative to the first RF tracking coil; and
        a second plurality of lumens.

2. The catheter device of claim 1, wherein a first inner lumen of the first plurality of lumens comprises a power supply and a second inner lumen of the first plurality of lumens comprises a cooling system for the ultrasonic transducer at the catheter device tip.

3. The catheter device of claim 1, wherein the inner catheter and the outer catheter have a bend radius of no more than about 2 cm.

4. The catheter device of claim 1, wherein the at least two guide wires are placed in opposing outer lumens of the plurality of lumens.

5. The catheter device of claim 4, wherein the at least two guide wires comprises nitinol.

6. The catheter device of claim 1, wherein the inner catheter further comprises a third RF tracking coil proximal the ultrasonic transducer relative to the first RF tracking coil.

7. The catheter device of claim 1, further comprising a plurality of ultrasonic transducers controllable to emit ultrasonic energy in a select pattern.

8. The catheter device of claim 1, wherein the inner catheter comprises polyether ether ketone.

9. A system for magnetic resonance imaging compatible ablative treatment of a target site, comprising:
    the catheter device of claim 1;
    a magnetic resonance imaging (MRI) system capable of detecting the RF tracking coils; and
    a 3-dimensional modeling and guidance system having a 3-dimensional model of the target site and in communication with the MRI system to provide an indication of a position of the catheter device with respect to the target site.

10. The catheter device of claim 1, wherein the catheter device tip has a different durometer than a proximal end of the catheter device.

11. The catheter device of claim 1, wherein a durometer of the catheter device ranges from 70D to 35D.

12. The catheter device of claim 1, wherein the rigid platform comprises ceramic.

13. The catheter device of claim 1, further comprising a plurality of magnetic resonance (MR) contrast markers integrated into the inner catheter at two or more locations along the inner catheter.

14. The catheter device of claim 1, wherein the ultrasonic transducer comprises one of a flat transducer assembly or a curvilinear transducer assembly.

15. The catheter device of claim 1, wherein the catheter device has an outside diameter of less than 0.1".

16. A method for ablating myocardium to treat cardiac rhythm conditions comprising:
    positioning, in proximity to myocardium, via transarterial, endovenous, transseptal atrial, or transaortic endoventricular access, a catheter device, the catheter device comprising:
        an inner catheter comprising:
            an ultrasonic transducer mounted on a rigid platform disposed within the inner catheter at a distal end of the catheter device defining a catheter device tip;
            a first radiofrequency (RF) tracking coil integrated within the inner catheter; and
            a first plurality of lumens; and
        an outer catheter surrounding the inner catheter, the outer catheter concentric with the inner catheter and comprising:
            at least two guide wires;
            a second RF tracking coil integrated within the outer catheter provided at a location proximal the ultrasonic transducer relative to the first RF tracking coil; and
            a second plurality of lumens;
    determining a position and an orientation of the catheter device, using the RF tracking coils, the RF tracking coils providing a real time localized signal;
    guiding the catheter device, using the at least two guide wires, based upon the position and the orientation of the catheter device, to a portion of a ventricular wall defining a treatment zone of the myocardium; and
    rotating and directing the catheter device tip to point the ultrasonic transducer at the treatment zone, transmitting high-intensity ultrasound energy to selectively target and ablate the treatment zone under magnetic resonance (MR) guidance.

17. The method of claim 16, wherein the position of the catheter device is determined in real time through at least one of:
pulse sequence application;
incorporation of multi-slice imaging, and
MR temperature monitoring.

18. The method of claim 9, wherein a depth of the treatment zone is about 0-20 mm.

19. The method of claim 16, wherein the ultrasonic transducer operates at a frequency of about 7-12 MHz at an intensity level of 10-15 W/cm$^2$.

\* \* \* \* \*